US012599407B2

(12) United States Patent
Scheib et al.

(10) Patent No.: US 12,599,407 B2
(45) Date of Patent: Apr. 14, 2026

(54) SYSTEM AND METHOD TO MEASURE UTERINE WALL THICKNESS

(71) Applicant: Cilag GmbH International, Zug (CH)

(72) Inventors: Charles J. Scheib, Loveland, OH (US); Tracey A. Morley, Sunnyvale, CA (US); Matthew T. Hill, Norwood, OH (US)

(73) Assignee: Cilag GmbH International, Zug (CH)

( * ) Notice: Subject to any disclaimer, the term of this patent is extended or adjusted under 35 U.S.C. 154(b) by 165 days.

(21) Appl. No.: 18/340,951

(22) Filed: Jun. 26, 2023

(65) Prior Publication Data

US 2024/0423669 A1     Dec. 26, 2024

(51) Int. Cl.
| | |
|---|---|
| *A61B 17/42* | (2006.01) |
| *A61B 5/107* | (2006.01) |
| *A61B 34/30* | (2016.01) |
| *A61B 34/37* | (2016.01) |

(52) U.S. Cl.
CPC ............ *A61B 17/42* (2013.01); *A61B 5/1076* (2013.01); *A61B 34/37* (2016.02); *A61B 2034/301* (2016.02); *A61B 2034/306* (2016.02); *A61B 2562/02* (2013.01)

(58) Field of Classification Search
CPC ............... A61B 17/42; A61B 17/4241; A61B 2017/4216; A61B 2034/301; A61B 2034/306; A61B 2562/02; A61B 34/37; A61B 5/1076
See application file for complete search history.

(56) References Cited

U.S. PATENT DOCUMENTS

| | | | |
|---|---|---|---|
| 9,743,955 | B2 | 8/2017 | Hill et al. |
| 9,763,741 | B2 | 9/2017 | Alvarez et al. |
| 9,788,859 | B2 | 10/2017 | Parys |
| 10,166,082 | B1 | 1/2019 | Hariri et al. |
| 10,464,209 | B2 | 11/2019 | Ho et al. |
| 10,639,072 | B2 | 5/2020 | Ahluwalia |
| 10,667,875 | B2 | 6/2020 | DeFonzo et al. |
| 10,765,303 | B2 | 9/2020 | Graetzel et al. |
| 10,827,913 | B2 | 11/2020 | Ummalaneni et al. |
| 10,881,280 | B2 | 1/2021 | Baez, Jr. |
| 10,898,277 | B2 | 1/2021 | Srinivasan et al. |
| 11,058,493 | B2 | 7/2021 | Rafii-Tari et al. |

(Continued)

*Primary Examiner* — Mohamed G Gabr
*Assistant Examiner* — Khoa Tan Le
(74) *Attorney, Agent, or Firm* — FBT Gibbons LLP

(57) ABSTRACT

A system includes a control console, a laparoscopic instrument, and a uterine manipulator. The laparoscopic instrument includes a first proximity sensor element. The uterine manipulator includes a base and a shaft extending distally from the base. The shaft includes a distal end dimensioned to be inserted into the uterus of a patient and a second proximity sensor element located at the distal end. The proximity sensor elements are configured to cooperatively generate a distance signal indicating a distance between the proximity sensor elements. The control console is configured to receive the distance signal from either the first proximity sensor element or the second proximity sensor element and calculate a corresponding distance between the proximity sensor elements. The control console is configured to compare the corresponding distance with a threshold distance and generate an alert signal when the corresponding distance is smaller than the threshold distance.

20 Claims, 18 Drawing Sheets

(56) References Cited

U.S. PATENT DOCUMENTS

| | | | |
|---|---|---|---|
| 11,090,082 B2 | 8/2021 | Weihe et al. | |
| 2018/0049829 A1* | 2/2018 | Yates | A61B 34/30 |
| 2021/0100584 A1 | 4/2021 | Einarsson | |
| 2021/0267692 A1* | 9/2021 | Lennartz | A61B 34/20 |
| 2023/0076998 A1* | 3/2023 | Scheib | A61B 17/42 |

* cited by examiner

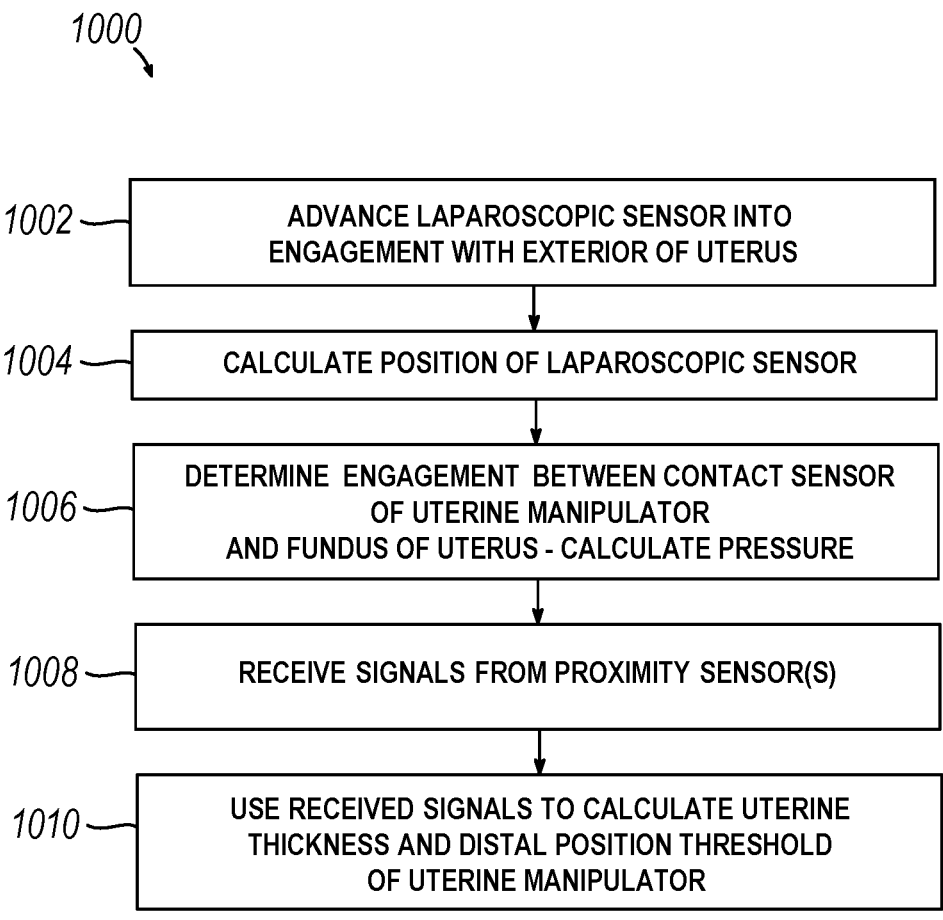

_1000_

1002 — ADVANCE LAPAROSCOPIC SENSOR INTO ENGAGEMENT WITH EXTERIOR OF UTERUS

1004 — CALCULATE POSITION OF LAPAROSCOPIC SENSOR

1006 — DETERMINE ENGAGEMENT BETWEEN CONTACT SENSOR OF UTERINE MANIPULATOR AND FUNDUS OF UTERUS - CALCULATE PRESSURE

1008 — RECEIVE SIGNALS FROM PROXIMITY SENSOR(S)

1010 — USE RECEIVED SIGNALS TO CALCULATE UTERINE THICKNESS AND DISTAL POSITION THRESHOLD OF UTERINE MANIPULATOR

FIG. 10

SYSTEM AND METHOD TO MEASURE UTERINE WALL THICKNESS

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endoluminal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

During a hysterectomy procedure, a colpotomy may be performed at the cervicovaginal junction. Such procedures may include the use of a uterine manipulator that includes a colpotomy cup or similar structure. Examples of instruments that may be used during a hysterectomy procedure are described in U.S. Pat. No. 9,743,955, entitled "Intracorporeal Transilluminator of Tissue Using LED Array," issued Aug. 29, 2017; U.S. Pat. No. 9,788,859, entitled "Uterine Manipulators and Related Components and Methods,"

issued Oct. 17, 2017; U.S. Pat. No. 10,639,072, entitled "Uterine Manipulator," issued May 5, 2020; U.S. Pat. No. 11,090,082, entitled "Colpotomy Systems, Devices, and Methods with Rotational Cutting," issued Aug. 17, 2021; and U.S. Pub. No. 2021/0100584, entitled "Uterine Manipulator," published Apr. 8, 2021, issued as U.S. Pat. No. 12,096,960 on Sep. 24, 2024.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 10 depicts a flowchart of an example of a method for a control console of the table-based robotic system of FIG. 1 to calculate a uterine thickness and a distal position threshold of the shaft of the uterine manipulator instrument of FIG. 8.

DETAILED DESCRIPTION

I. Overview of Example of Robotic Surgical System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the clinician. Additionally, the system may provide the clinician with the ability to perform the procedure from an ergonomic position without the need for awkward arm motions and positions. Still further, the system may provide the clinician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Table

Figure 1:
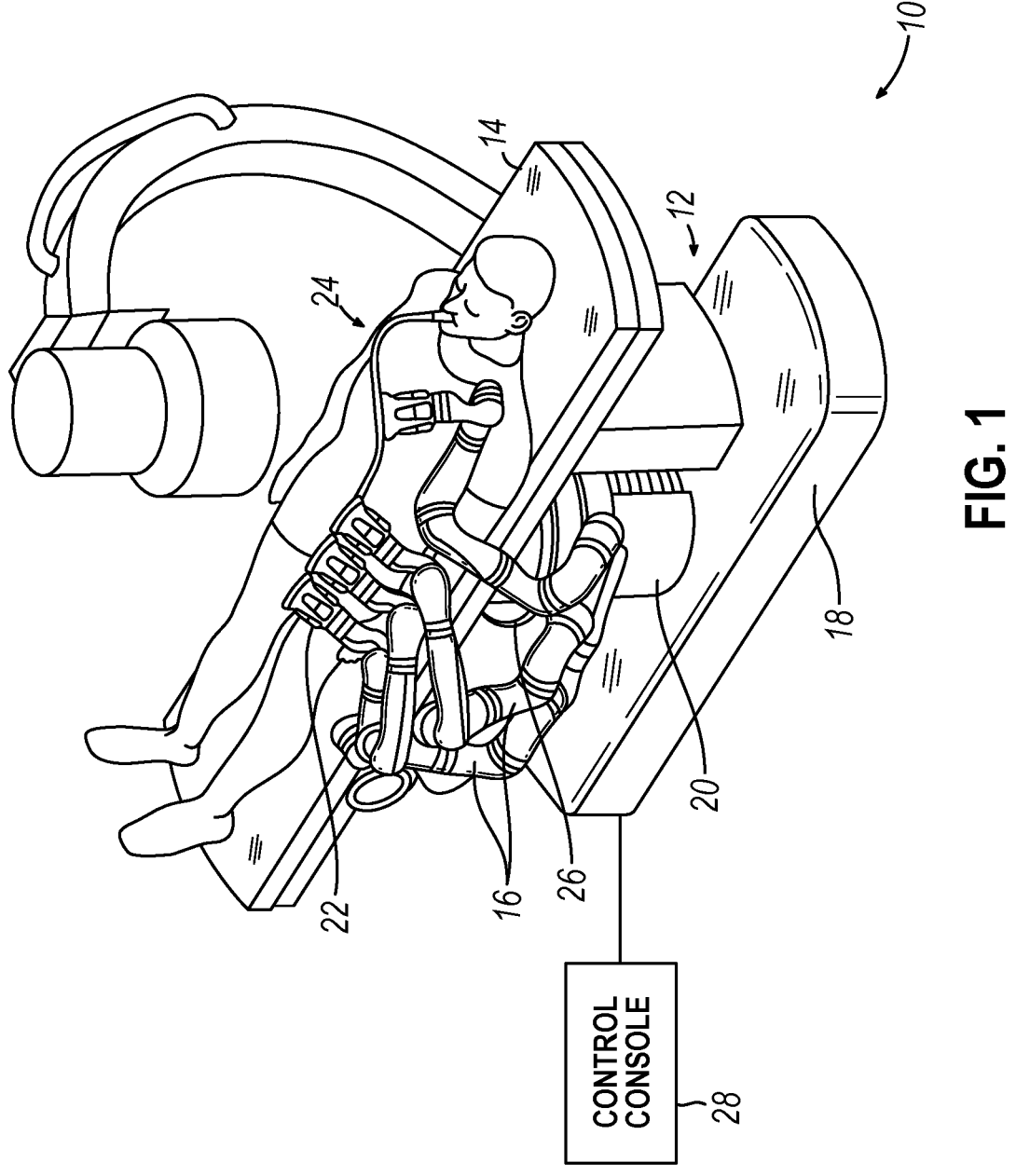
FIG. 1 depicts a perspective view of an example of a table-based robotic system that includes a control console and a plurality of robotic arms.

FIG. 1 illustrates an example of a robotic surgical system (10). Robotic surgical system (10) includes a support structure (12) for supporting a platform (14) (shown as a "table" or "bed") over the floor and one or more robotic arms (16). Support structure (12) includes a base (18) and a column (20). Column (20) structurally supports platform (14), and provides a path for vertical translation of the carriages. In some versions, a table base may stow and store robotic arms (16) when not in use. Column (20) of the present example also includes a ring-shaped carriage (26), from which robotic arms (16) are based. A control console (28) is coupled with robotic surgical system (10).

Robotic arms (16) are shown as part of a table-mounted system, but in other configurations, robotic arms (16) may be mounted in a cart, ceiling or sidewall, or other suitable support surface. Robotic arms (16) are shown as extending from column (20) via carriage (26). However, robotic arms (16) may be coupled with robotic surgical system (10) using a variety of suitable structures. While robotic arms (16) are all shown as being positioned on one side of the patient in FIG. 1, other configurations may position robotic arms (16) on both sides of the patient, between the legs of the patient, and/or in any other suitable locations. Tool drivers (22) are positioned at distal ends of robotic arms (16) in the present example. Tool drivers (22) are operable to manipulate one or more surgical instruments (24), as will be described in greater detail below.

B. Example of a Robotic Arm, Tool Drive, and Tool

Figure 2:
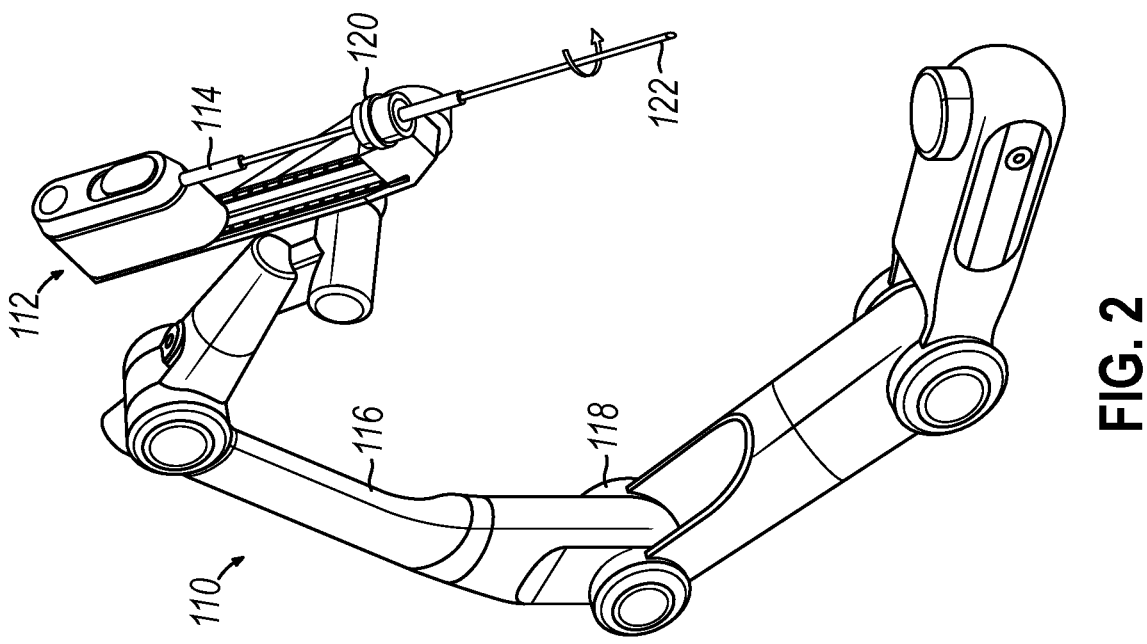
FIG. 2 depicts a perspective view of an example of a robotic arm, an example of a tool drive, and an example of an instrument, each configured for use with the table-based robotic system of FIG. 1.

FIG. 2 shows an example of a robotic arm (110), a tool driver (112), and an instrument (114), which may be incorporated into robotic surgical system (10) in place of a robotic arm (16), a tool driver (22), and a surgical instrument (24) that are shown in FIG. 1. Additional examples of robotic arms, a tool drivers, and a surgical instruments are shown and described in U.S. Pat. No. 10,166,082, entitled "System and Method for Controlling a Robotic Wrist," issued Jan. 1, 2019, the disclosure of which is incorporated by reference herein, in its entirety.

As shown in FIG. 2, robotic arm (110) includes a plurality of links (116) and a plurality of joints (118) for actuating links (116) relative to one another. Tool driver (112) is attached to the distal end of robotic arm (110). Tool driver (112) includes a cannula (120) coupled to the end of tool driver (112), to receive and guide instrument (114). Instrument (114) may include an endoscope, a laparoscope, a stapler, graspers, an ultrasonic instrument, an RF electrosurgical instrument, or any other suitable kind of instrument. Instrument (114) is inserted into the patient via cannula (120). The distal end of instrument (114) includes an end effector (122). End effector (122) is configured to interact with the patient (e.g., providing visualization, stapling, grasping, ultrasonic cutting and/or sealing, electrosurgical cutting and/or sealing, etc.).

Joints (118) of robotic arm (110) may be actuated to selectively position and orient tool driver (112), which actuates the end effector (122) for robotic surgeries. Joints (118) may include various types, such as a pitch joint or a roll joint, which may substantially constrain the movement of the adjacent links (116) around certain axes relative to other links (116). Each joint (118) represents an independent degree of freedom available to robotic arm (110). A multitude of joints (118) result in a multitude of degrees of freedom, allowing for "redundant" degrees of freedom. Redundant degrees of freedom allow the robotic arms (110) to position their respective end effectors (122) at a specific position, orientation, and trajectory in space using different positions links (116) and angles of joints (118). This allows for the system to position and direct an instrument (114) from a desired point in space while allowing the clinician to move joints (118) into a clinically advantageous position away from the patient to create greater access, while avoiding collisions of robotic arms (110).

Movement of robotic arm (110) may be controlled by a clinician via suitable portions of control console (28). Control console (28) may include any suitable components as would be apparent to one skilled in the art in view of the teachings herein, such as processor(s), memory, storage, visual display units(s), controllers, input devices, point and click devices, monitoring units, mechanical pumps, generators, etc. In some instances, one or more portions of control console (28) utilized by the clinician to control movement of robotic arm (110) are located outside the surgical theater where robotic arms (110) and patient are located. Control console (28) may include separate modules that are in communication with each other but located at different areas/rooms/geographical locations. For example, control console (28) may include a surgeon's control console configured to be utilized by the clinician to control movement of robotic arm(s) (110), and also include a designated control tower located near the platform (14) for use by clinicians within the surgical theater.

II. Example of Robotically Controlled Uterine Manipulator

In some conventional hysterectomy procedures, a first clinician may serve in a role of forming incisions and performing other laparoscopic operations to remove the uterus of a patient, while a second clinician may serve in a role of manipulating the position and orientation of the uterus of the patient to facilitate the operations being performed by the first clinician. Such team-based procedures may require clear communication between the first clinician and the second clinician, with the first clinician instructing the second clinician on desired positioning and orientation of the uterus, and with the second clinician responding in a timely and accurate fashion. In some scenarios, such communications may break down or otherwise yield undesirable results, such as the second clinician not precisely positioning or orienting the uterus when and where the first clinician wishes. It may therefore be desirable to provide a robotic system that is capable of performing at least part of the role of the second clinician, such that the robotic system may at least partially control the position and orientation of the uterus based on the desire of the first clinician. Examples of how a robotic system may provide uterine manipulation are described in greater detail below. The following examples may be readily incorporated into robotic system (10) described herein; or in any other suitable robotic system as would be apparent to one skilled in the art in view of the teachings herein.

Figure 3:
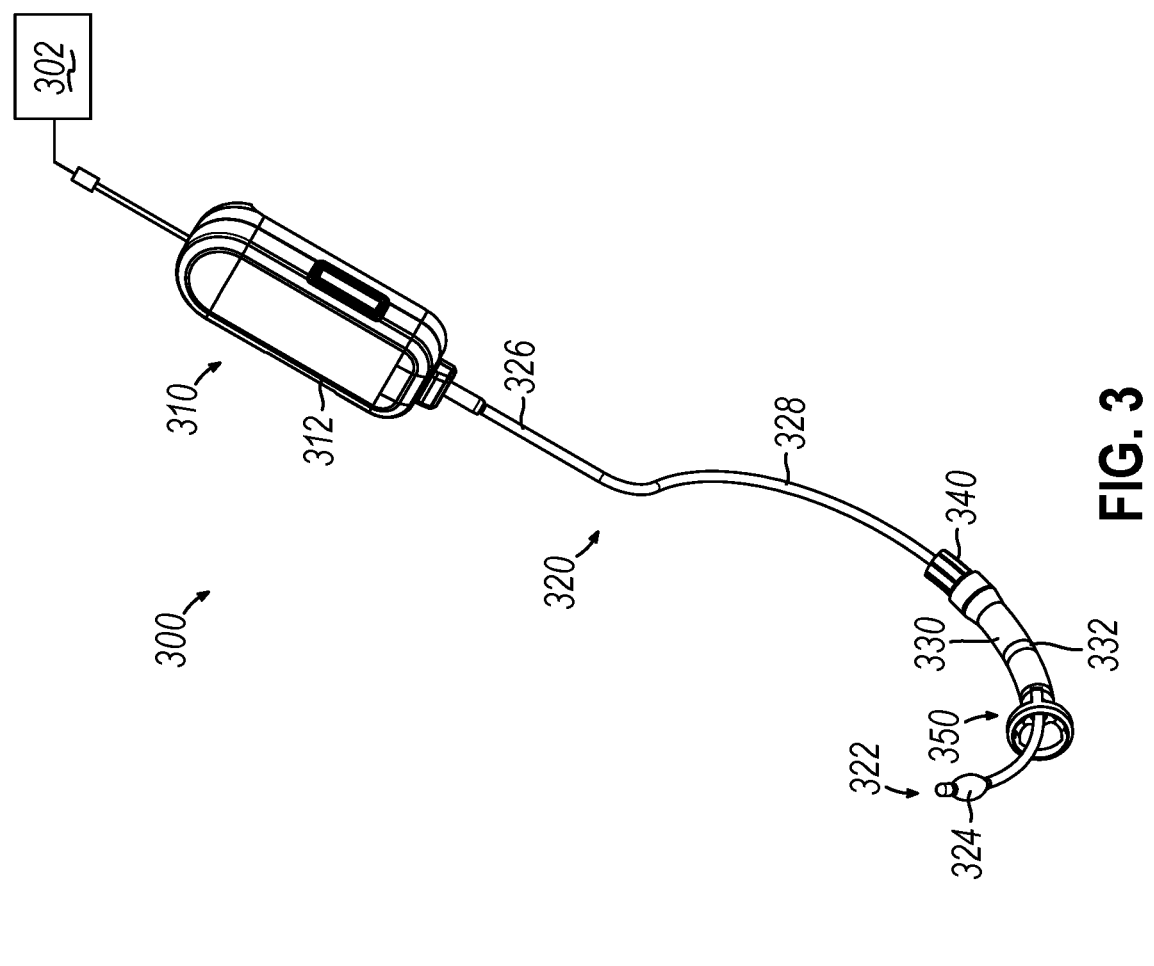
FIG. 3 depicts a perspective view of an example of a uterine manipulator that may be operatively attached to the tool drive of FIG. 2.

FIG. 3 shows an example of a uterine manipulator (300) that may be secured to a robotic arm (100) shown in FIG. 2 in replacement of instrument (114).

Uterine manipulator (300) may be removably coupled with tool driver (112) and/or cannula (120), such that robotic arm (110) may selectively position and orient uterine manipulator (300) in relation to a patient by driving robotic arm (110). As best seen in FIG. 3, uterine manipulator (300) of the present example includes a tool driver interface (310), a shaft (320), a sleeve (330), a sleeve locking ring (340), and a colpotomy cup (350). Tool driver interface (310) includes a base (312). Base (312) is configured to removably couple with tool driver (112) of robotic arm (110) to thereby secure uterine manipulator (300) with robotic arm (110). In some instance, base (312) is configured to be grasped and controlled by a user, in addition to, or as an alternative to, being configured to removably couple with tool driver (112) of robotic arm (110).

A linear portion (326) of shaft (320) extends distally from base (312) may extend through cannula (120) when uterine manipulator (300) is coupled to robotic arm (110). In some instances, linear portion (326) of shaft (320) slidably extends through cannula (120); while in other instances linear portion (326) of shaft (320) may be temporarily secured to cannula (120). By way of example only, base (312) and tool driver (112) may include complementary bayonet fitting features, complementary threading, complementary snap-fit features, and/or any other suitable kinds of structures to provide a removable coupling. Shaft (320) is configured to couple with a pressurized fluid source (302). Pressurized fluid source (302) may contain pressurized air, pressurized saline, or any other suitable kind of pressurized fluid. The pressurized fluid may be used to selectively inflate balloons (324, 332), which will be described in greater detail below.

Shaft (320) of the present example extends distally from base (312). Shaft (320) includes proximal linear portion (326) and distal curved portion (328). In some versions, shaft (320) is rigid. In some other versions, shaft (320) is flexible yet resiliently biased to assume the curved configuration shown. Any suitable biocompatible material(s) may be used to form shaft (320), including but not limited to metallic materials, plastic materials, and combinations thereof. An inflatable balloon (324) is positioned near distal end (322) of shaft (320). Balloon (324) may be formed of an extensible material or a non-extensible material. The interior of shaft (320) includes one or more lumen(s) that are configured to communicate pressurized fluid from pressurized fluid source (302) to balloon (324). While balloon (324) is positioned near distal end (322) of shaft (320) in the present example, other versions may include a different kind of expandable member. By way of example only, an alternative expandable member may include a mechanically expandable component such as an expandable mesh structure, an expanding umbrella-like structure, or any other suitable kind of expandable structure or assembly. In some versions, distal end (322) of shaft (320) may also include an illuminating element (e.g., one or more LEDs, a lens illuminated by one or more optical fibers, etc.). In such versions, one or more wires, optical fibers, and/or other components may extend along the length of shaft (320) to couple with a source of electrical power, a source of light, etc.

Figure 6A:
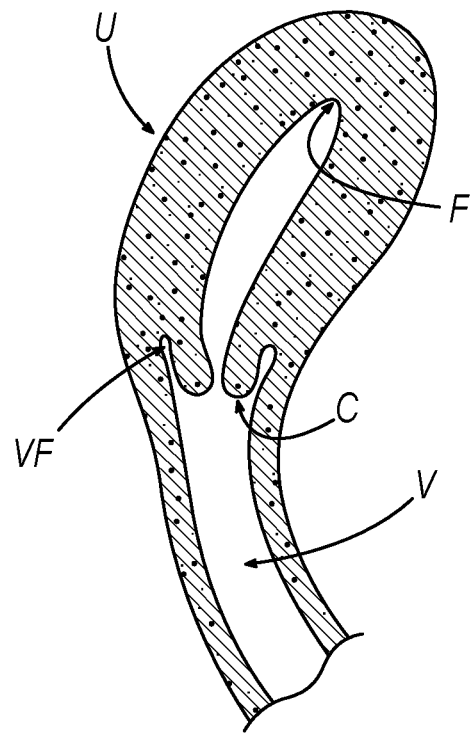
FIG. 6A depicts a mid-sagittal cross-sectional view of a vagina and uterus.
Figure 6B:
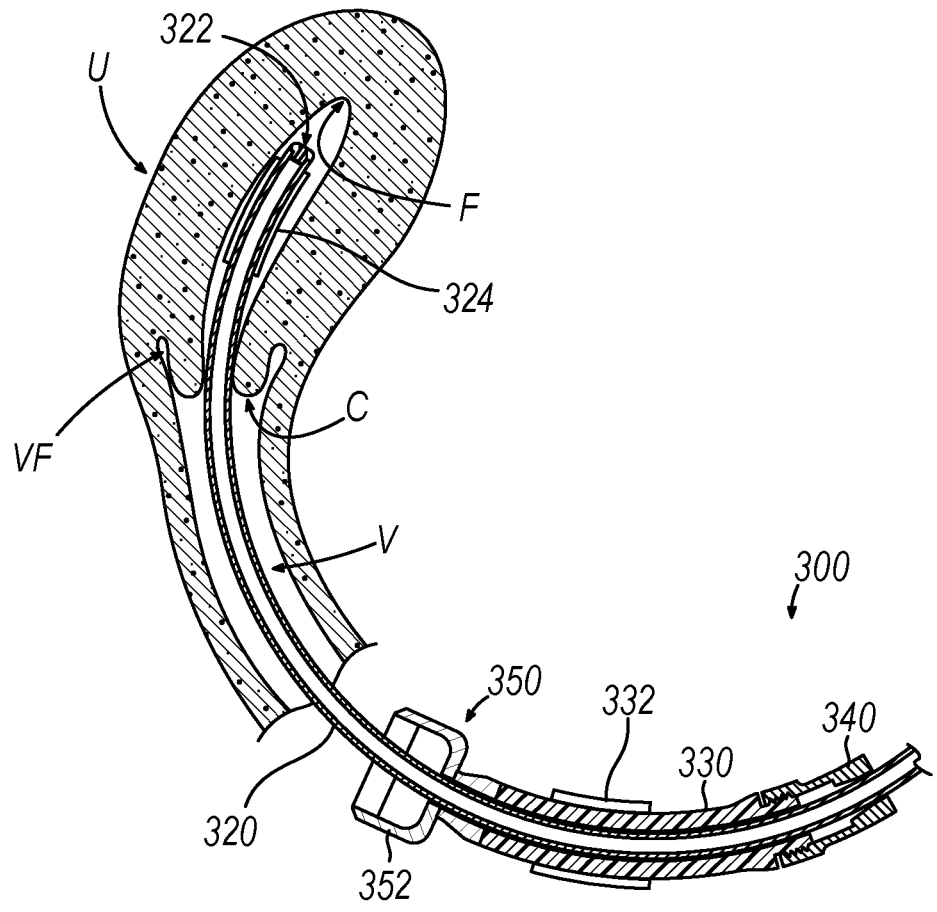
FIG. 6B depicts a mid-sagittal cross-sectional view of the vagina and uterus of FIG. 6A, with the shaft of the uterine manipulator instrument of FIG. 3 inserted through the vagina into the uterus, with a balloon of the uterine manipulator instrument in a deflated state, and with a sleeve of the uterine manipulator instrument in a proximal position.
Figure 6C:
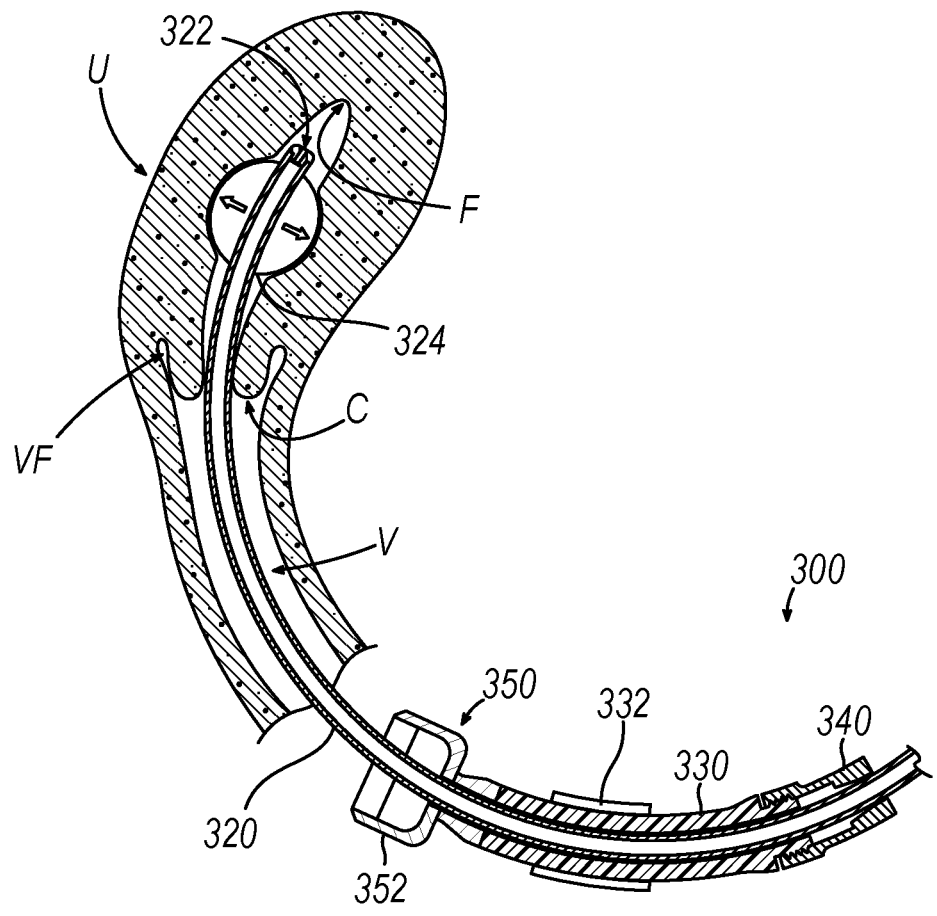
FIG. 6C depicts a mid-sagittal cross-sectional view of the vagina and uterus of FIG. 6A, with the shaft of the uterine manipulator instrument of FIG. 3 inserted through the vagina into the uterus, with the balloon of the uterine manipulator instrument in an inflated state, and with the sleeve of the uterine manipulator instrument in the proximal position.
Figure 6D:
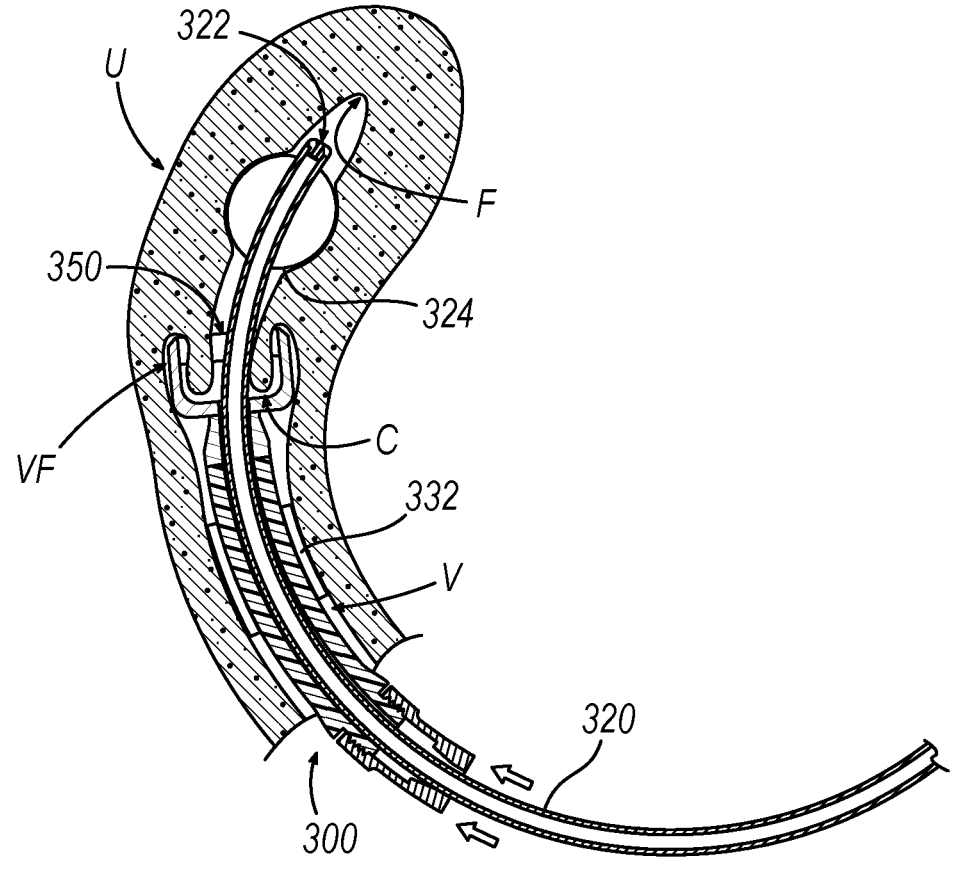
FIG. 6D depicts a mid-sagittal cross-sectional view of the vagina and uterus of FIG. 6A, with the shaft of the uterine manipulator instrument of FIG. 3 inserted through the vagina into the uterus, with the balloon of the uterine manipulator instrument in the inflated state, with the sleeve of the uterine manipulator instrument in a distal position such that the colpotomy cup of the sleeve is engaged with the cervix, and with a balloon of the sleeve in a deflated state.
Figure 6E:
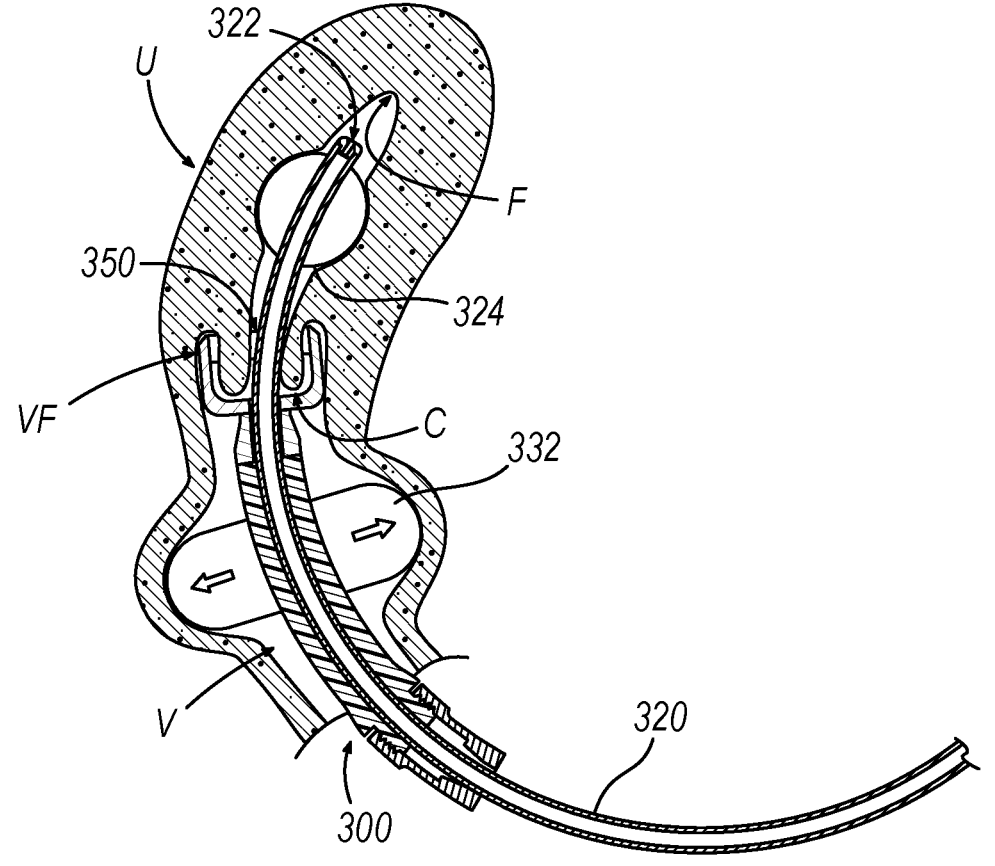
FIG. 6E depicts a mid-sagittal cross-sectional view of the vagina and uterus of FIG. 6A, with the shaft of the uterine manipulator instrument of FIG. 3 inserted through the vagina into the uterus, with the balloon of the uterine manipulator instrument in the inflated state, with the sleeve of the uterine manipulator instrument in the distal position such that the colpotomy cup of the sleeve is engaged with the cervix, and with the balloon of the sleeve in an inflated state.

Sleeve (330) is slidably coupled to distal curved portion (328) of shaft (320), such that sleeve (330) may slide along shaft (320) from a proximal position (FIGS. 6B-6C) to any number of distal positions (FIGS. 3, 6D-6E). Sleeve (330) is generally cylindraceous and rigid; and extends along a curved axis such that the curved profile complements the curved profile of curved portion (328) of shaft (320). Sleeve (330) may be formed of plastic, metal, and/or any other suitable biocompatible material(s), including combinations of materials. Locking ring (340) is rotatably secured to the proximal end of sleeve (330), while colpotomy cup (350) is fixedly secured to the distal end of sleeve (330). An inflatable balloon (332) is positioned along sleeve (330), between locking ring (340) and colpotomy cup (350). Balloon (332) may be formed of an extensible material or a non-extensible material. The interior of sleeve (330) includes one or more lumen(s) that are configured to communicate pressurized fluid from pressurized fluid source (302) to balloon (332). Such a lumen or lumens may be coupled with pressurized fluid source (302) via a flexible tube (not shown). In some versions, one or more lumens or tubes within shaft (320) provide at least part of the fluid pathway between balloon (332) and pressurized fluid source (302).

Locking ring (340) is operable to selectively secure the position of sleeve (330) along the length of shaft (320). For instance, locking ring (340) may be rotated to a first angular position relative to sleeve (330) to provide an unlocked state where sleeve (330) may be freely translated along shaft (320). Locking ring (340) may then be rotated to a second angular position relative to sleeve (330) to provide a locked state where the position of sleeve (330) along shaft (320) is secured until locking ring (340) is rotated back to the first angular position. By way of example only, locking ring (340) may include one or more frictional braking structures that selectively engage shaft (320) to thereby provide the locked state. Alternatively, locking ring (340) may selectively engage shaft (320) in any other suitable fashion.

Figure 4:
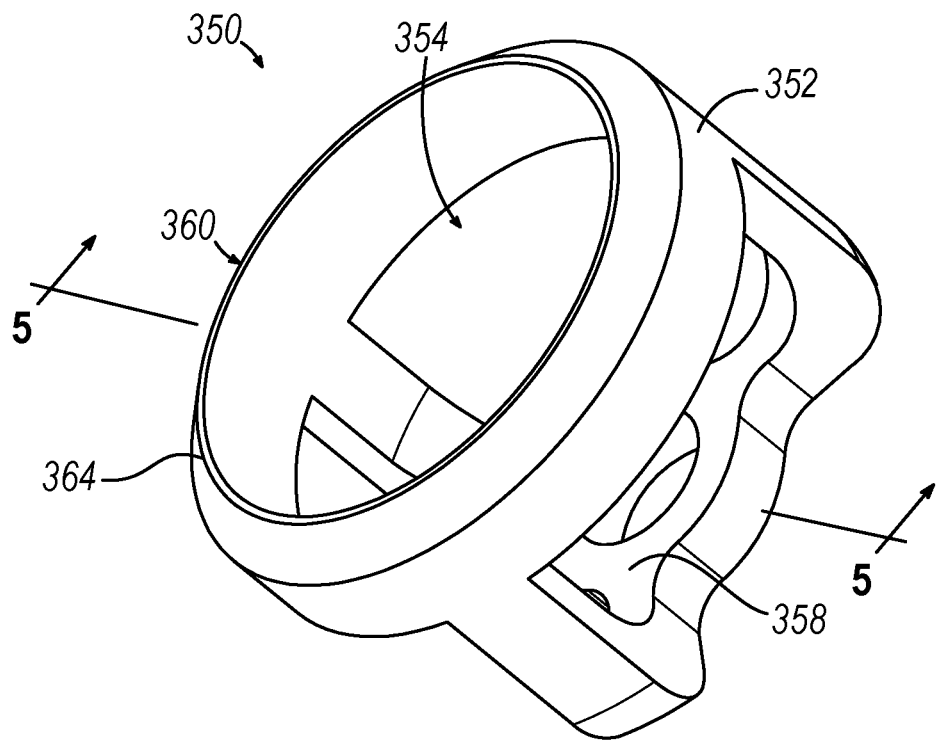
FIG. 4 depicts a perspective view of a colpotomy cup of the uterine manipulator of FIG. 3.
Figure 5:
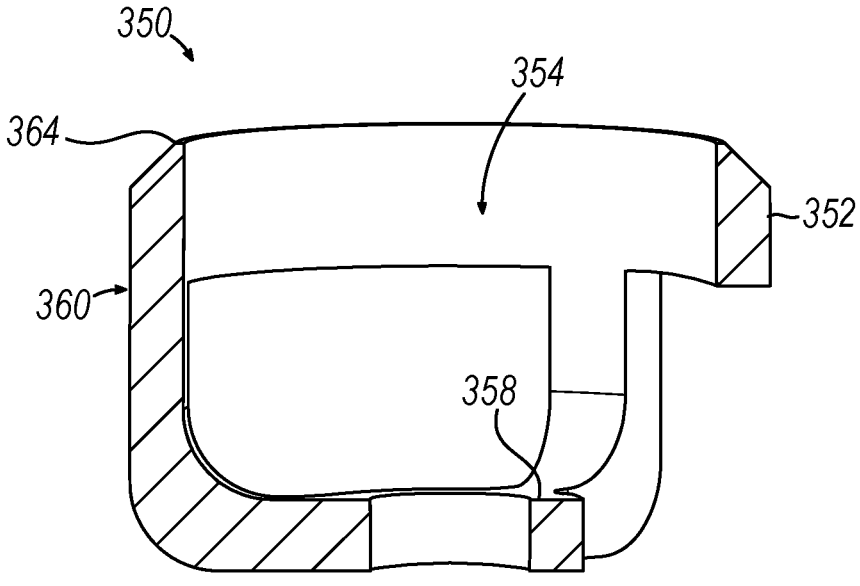
FIG. 5 depicts a cross-sectional view of the colpotomy cup of FIG. 4, taken along line 5-5 of FIG. 4.

FIGS. 4-5 show colpotomy cup (350) in greater detail. As shown, colpotomy cup (350) of the present example includes a body (352) defining an interior space (354). Body (352) further includes a floor (358) at the bottom of interior space (354) and an open distal end (360). A plurality of lateral openings (356) are in communication with interior space (354). Distal end (360) includes a distally presented annular edge (364). Colpotomy cup (350) may be formed of plastic, metal, and/or any other suitable biocompatible material(s), including combinations of materials.

FIGS. 6A-6E show an example of a procedure in which uterine manipulator (300) is used. As shown in FIG. 6A, the anatomical context in which uterine manipulator (300) is used includes a vagina (V) and uterus (U) of a patient. As shown in FIG. 6B, distal end (322) of shaft (320) is inserted through the vagina (V) and into the uterus (U) via the cervix (C), while sleeve (330) is in a proximal position along shaft (320). Balloon (324) is in a deflated state during this stage of insertion. In some versions, uterine manipulator (300) is fully decoupled from robotic arm (110) during the process leading up to the stage shown in FIG. 6B, such that uterine manipulator (300) is advanced to this state manually by a human operator grasping a proximal portion of uterine manipulator (300) (e.g., grasping a proximal portion of shaft (320), grasping base (312), and/or grasping some other part of uterine manipulator (300)). In such scenarios, uterine manipulator (300) may be coupled with robotic arm (110) after reaching the stage shown in FIG. 6B.

In some other versions, uterine manipulator (300) is already coupled with robotic arm (110) before reaching the stage shown in FIG. 6B; and robotic arm (110) is used to guide and drive uterine manipulator (300) to the position shown in FIG. 6B. As yet another variation, some versions may allow a human operator to guide and drive uterine manipulator (300) to the position shown in FIG. 6B while uterine manipulator (300) is coupled with robotic arm (110), such that robotic arm (110) does not restrict manual movement of uterine manipulator (300) leading up to the stage shown in FIG. 6B. In still other versions, uterine manipulator (300) may be controlled by a human operator throughout the entire operation such that uterine manipulator (300) does not couple with robotic arm (110).

Regardless of the stage at which uterine manipulator (300) is coupled with robotic arm (110), robotic arm (110) may be positioned in various suitable ways relative to the patient while uterine manipulator (300) is inserted in the patient. In some scenarios, robotic arm (110) crosses over the top of one of the patient's legs from the side, to assist in positioning uterine manipulator (300). In some other scenarios (e.g., when the patient's legs are supported by stirrups), robotic arm (110) crosses under the bottom of one of the patient's legs from the side, to assist in positioning uterine manipulator (300). In still other scenarios, robotic arm (110) is positioned between the patient's legs from underneath, such that robotic arm (110) does not cross over or under either of the patient's legs. Alternatively, robotic arm (110) may have any other suitable spatial and positional relationship with respect to the patient.

In the present example, uterine manipulator (300) is advanced distally until distal end (322) of shaft (320) reaches the fundus (F) of the uterus (U). The operator may determine that distal end (322) has reached the fundus (F) via tactile feedback (e.g., such that the operator can feel sudden resistance to further advancement of shaft (320)). In some cases where distal end (322) contacts the fundus (F), distal end (322) may remain in contact with fundus (F) throughout the rest of the procedure shown in FIGS. 6B-6E. In some other versions, distal end (322) may be slightly backed out proximally, such that distal end (322) does not contact fundus (F) throughout the rest of the procedure shown in FIGS. 6B-6E.

After reaching the state shown in FIG. 6B, balloon (324) may be inflated as described above; and as shown in FIG. 6C. In some cases, balloon (324) is inflated to a point where balloon (324) bears outwardly against the sidewall of the uterus (U). In any case, the inflated balloon (324) may stabilize the distal portion of shaft (320) relative to the uterus (U). Specifically, the inflated balloon (324) may prevent shaft (320) from exiting proximally from the uterus (U) via the cervix (C). Balloon (324) may thus serve as a distally-positioned anchor structure for uterine manipulator (300). The inflated balloon (324) may also provide sufficient engagement between shaft (320) and the uterus (U) to allow use of shaft (320) to reposition and reorient the uterus (U) as described herein.

With balloon (324) in the inflated state the operator may advance sleeve (330) distally along shaft (320) to the position shown in FIG. 6D. In the present example, this is performed by a human operator manually advancing sleeve (330) distally along shaft (320). In some other versions, this may be performed by a robotic operator robotically advancing sleeve (330) distally along shaft (320). As shown, sleeve (330) is advanced distally to a point where distal end (360) is firmly seated in the vaginal fornix (VF). The cervix (C) is received in interior space (354) of body (352). At this stage, the longitudinal position of sleeve (330) along shaft (320) is locked in place via locking ring (340). Specifically, the operator grasps locking ring (340) and rotates locking ring (340) about shaft (320) to firmly lock the position of sleeve (330) along shaft (320). In the present example, this is performed by a human operator, though it may be performed by a robotic operator in other versions. With the position of sleeve (330) locked in place against shaft (320), the position of uterine manipulator (300) is substantially fixed relative to the vagina (V), the cervix (C), and the uterus (U). While balloon (324) serves as a distally-positioned anchor structure for uterine manipulator (300), colpotomy cup (350) serves as a proximally-positioned anchor structure for uterine manipulator (300).

With the position of uterine manipulator (300) being fixed by the combination of balloon (324) and colpotomy cup (350), balloon (332) is inflated as shown in FIG. 6E. Balloon (332) bears outwardly against the sidewall of the vagina (V), thereby creating a fluid-tight seal against the sidewall of the vagina (V).

With uterine manipulator (300) being positioned and configured as shown in FIG. 6E, robotic arm (110) may be utilized to drive uterine manipulator (300) to various positions, to thereby re-orient and reposition the uterus (U) as desired by the clinician who is performing the rest of the medical procedure (e.g., hysterectomy). In some scenarios, the clinician who robotically controls robotic arm (110) to drive uterine manipulator (300) to position and orient the uterus (U) also uses the same robotic system to control instruments that are used to perform a surgical procedure associated with the uterus (U) (e.g., a hysterectomy).

As noted above, by allowing a surgeon to directly control the manipulation of the uterus (U) via robotic arm (110) and uterine manipulator (300), the process avoids potential confusion and inconsistency that might otherwise result in procedures where a human assistant is controlling a uterine manipulator based on commands from another human clinician. Moreover, once the uterus (U) has been manipulated to achieve the desired position and orientation, robotic arm (110) and uterine manipulator (300) may cooperate to maintain this position and orientation of the uterus (U) indefinitely. This may avoid scenarios where a human operator of a uterine manipulator (300) might inadvertently reposition or reorient the uterus (U) in the middle of a medical procedure. However, as also mentioned above, in some versions, uterine manipulator (300) may be properly controlled by a human operator throughout the entire procedure.

As noted above, one medical procedure that may be performed using robotic arm (110) and uterine manipulator (300) is a hysterectomy. In some versions of such a procedure, one or more cutting instruments are introduced laparoscopically via the patient's abdomen to approach the cervicovaginal junction from outside the uterus (U) and vagina (V). Such instrumentation may be controlled manually or robotically. In versions where the instrumentation is controlled robotically, the same robotic system may control the instrumentation and robotic arm (110). A cutting instrument may cut the uterus (U) away at the cervicovaginal junction, generally tracing around the circular perimeter defined by distal end (360) of colpotomy cup (350).

This cutting at the cervicovaginal junction will ultimately result in separation of the uterus (U) from the vagina (V); and the end of the vagina (V) may be appropriately closed at this point. During this process, the patient's abdomen may be insufflated with pressurized gas, and the pressurized insufflation gas may eventually reach the distal region of the vagina (V). In such scenarios, balloon (332) will provide sealed occlusion that is sufficient to prevent the pressurized insufflation gas from escaping out of the patient via the vagina (V).

While robotic arm (110) and uterine manipulator (300) are described in the foregoing example as being used in a hysterectomy, robotic arm (200) and uterine manipulator (300) may be used in any other suitable fashion and may be used in any other suitable procedures.

Figure 7A:
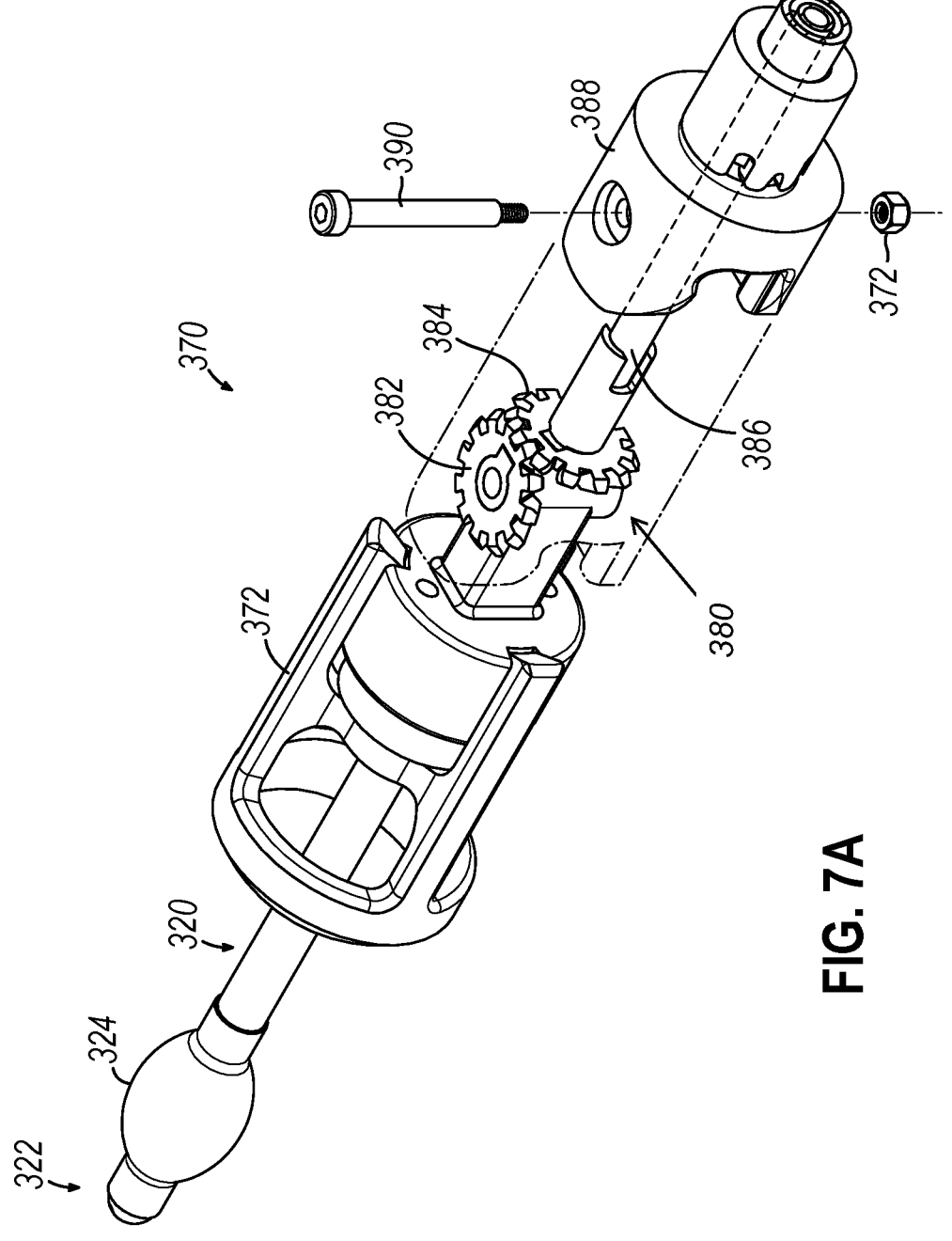
FIG. 7A depicts a partially exploded perspective view of an alternative colpotomy cup.
Figure 7B:
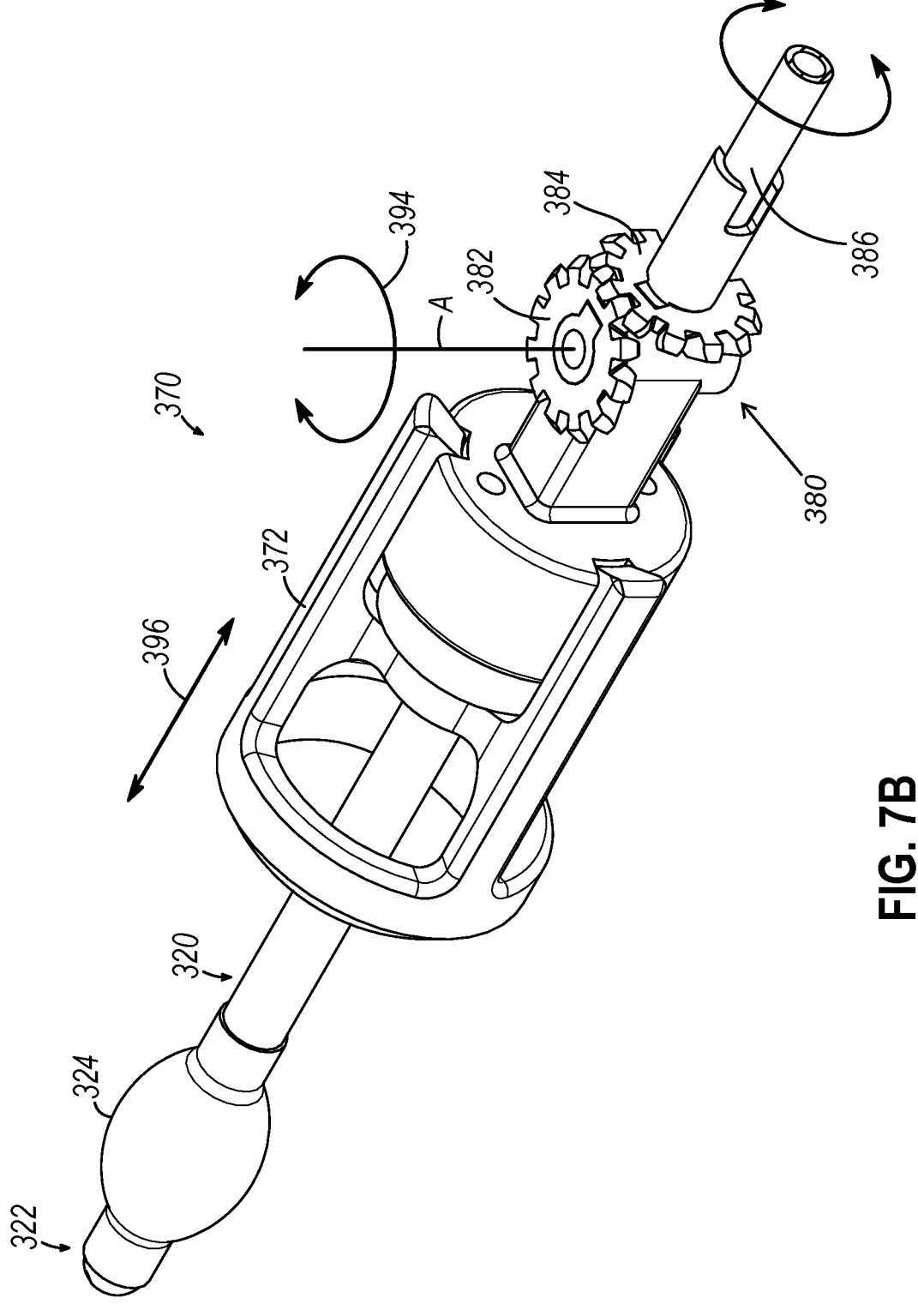
FIG. 7B depicts a perspective view of the of the colpotomy cup of FIG. 7A.

In some instances, it may be desirable to control the position and orientation of the uterus (U) without moving the proximal portion of uterine manipulator (300) relative to the patient. FIGS. 7A-7B show an alternative colpotomy cup (370) that may be readily incorporated into uterine manipulator (300) described above in replacement of colpotomy cup (350). Therefore, colpotomy cup (370) may translate into a suitable longitudinal position relative to shaft (320), as illustrated by arrow (396) in FIG. 7B, in order to suitably position colpotomy cup (370) relative to shaft (320) in accordance with the description herein.

Colpotomy cup (370) is substantially similar to colpotomy cup (370) described above, with differences elaborated below. In particular, colpotomy cup (370) includes an articulation drive assembly (380) configured to rotate body (372) of colpotomy cup (370) about articulation axis (A), as illustrated by arrow (394), relative to a proximal portion of shaft (320). Shaft (320) extends through colpotomy cup (370) such that rotation of colpotomy cup (370) about articulation axis (A) bends distal end (322) and balloon (324) of shaft (320). Therefore, articulation drive assembly (380) may be utilized to control the position and orientation of the uterus (U) via articulation of colpotomy cup (370) and distal end (322).

In the current example, articulation drive assembly (380) includes a first gear (382), a second gear (384) meshed with the first gear (382), a rotary driver (386) extending proximally within shaft (320) and attached to second gear (384), and a clevis body (388) housing gears (382, 384) via a pin (390) and nut (392). Pin (390) extends through an opening defined by first gear (382), a proximal portion of body (372), and clevis body (388).

Rotary driver (386) extends through clevis body (388) and is configured to rotate relative to clevis body (388) about its own axis. Rotary driver (386) is suitably attached to a rotating input (not shown) located at a proximal end of uterine manipular (300). Rotating input (not shown) is configured to drive rotation of rotary driver (386) about its own longitudinal axis, thereby driving rotation of second gear (384) relative to clevis body (388). Second gear (384) suitably meshes with first gear (382) such that rotation of second gear (384) via rotary driver (386) drives rotation of first gear (382) as indicated by the arrow (394). Therefore, second gear (384) may rotate first gear (382) in a first rotational direction, or an opposite, second, rotational direction. First gear (382) is suitably coupled to body (372) of colpotomy cup (370) such that rotation of first gear (382) drives rotation of body (372) about articulation axis (A) relative to clevis body (388) and the proximal portion of shaft (320), as indicated by arrow (394) shown in FIG. 7B. Therefore, an operator may utilize articulation drive assembly (380) in order to articulate distal end (322) of shaft (320) and colpotomy cup (370) relative to a proximal portion of shaft (320). Such articulation may be utilized when colpotomy cup (370) and shaft (320) are suitably attached to anatomy of a patient in order to position and orient the uterus (U) in accordance with the description herein.

III. Illustrative System and Method to Measure Uterine Wall Thickness and/or Instrument Location Relative to Uterine Wall As described above, and as shown between FIGS. 6A-6B, distal end (322) of shaft (320) is initially inserted through the vagina (V) and into the uterus (U) via the cervix (C) until reaching a suitable location adjacent to, or in contact with, fundus (F). In some instances, the depth or cavity length of the uterus (U) may be known prior to insertion of distal end (322) via a sounding process, where a sounding instrument is utilized to measure the depth or cavity length of the uterus (U). As also described above, after uterine manipulator (300) is suitably coupled to suitable anatomical structures (as illustrated in FIG. 6E), uterine manipulator (300) may be utilized (either manually or robotically) in order to manipulate the position and orientation uterus (U) to facilitate the operations being performed.

In some instances, distal end (322) of shaft (320) may be inadvertently over-inserted relative to adjacent anatomical structure. Such over-insertion may occur while initially inserting distal end (322), as shown between FIGS. 6A-6B, and/or while utilizing uterine manipulator (300) to position/orient uterus (U) in accordance with the description herein. Further, over-insertion may occur when uterine manipulator (300) is being manually controlled by a second clinician or robotically controlled by surgical system (10). Over-insertion of distal end (322) may potentially perforate, or otherwise undesirably damage, the uterus (U).

Therefore, it may be desirable to measure the distance between distal end (322) of shaft (320) and desired anatomical structures of the uterus (U) and/or measure forces generated by distal end (322) contacting desired anatomical structures of the uterus (U), such as the fundus (F). Further, in addition to measuring the distance between distal end (322) of shaft (320) and desired anatomical structures, it may be desirable to notify a clinician when distal end (322) is actuated past a pre-determined threshold relative to the desired anatomical structure, thereby indicating to a clinician that distal end (322) is close to being over-inserted. Additionally, and/or alternatively, in instances where uterine manipulator is controlled by robotic surgical system (10) and robotic arm (16, 110) is instructed to actuate distal end (322) past a pre-determined threshold relative to the desired anatomical structure, it may be desirable to geofence, or otherwise inhibit, movement of robotic arm (110, 16) coupled with uterine manipular (300), to thereby inhibit over-insertion when distal end (322). In addition to determining the depth or cavity length of the uterus (U), it may be beneficial to determine the wall thickness of the uterus (U), particularly at the fundus (F), to further reduce the risk of inadvertent perforation or other damage by uterine manipulator (300).

Figure 8:
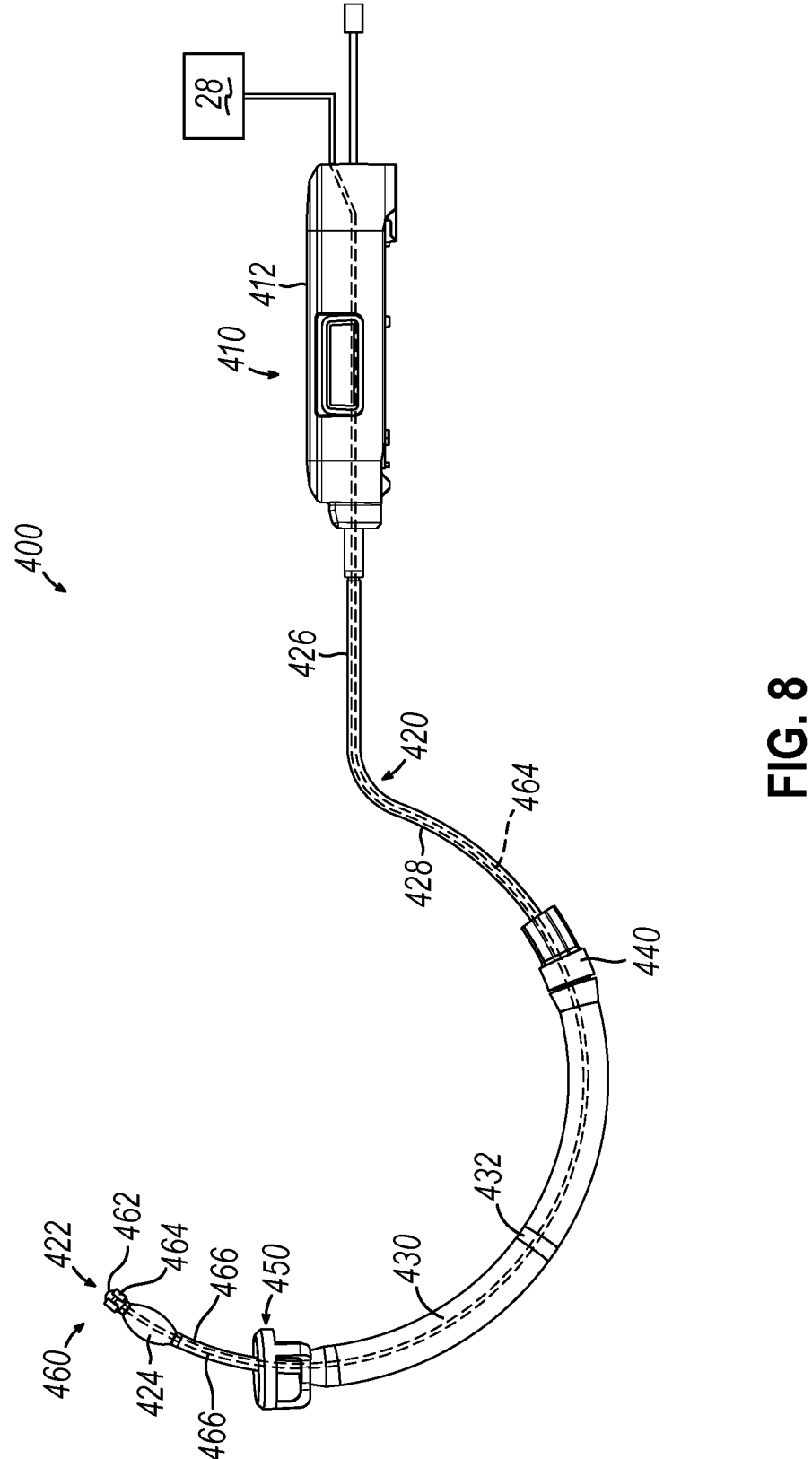
FIG. 8 depicts an elevational side view of an alternative uterine manipulator having a distal sensor assembly.

FIG. 8 shows an example of a uterine manipulator (400) that is configured to be used in conjunction with a laparoscopic instrument (470) (see FIGS. 9A-9E) and robotic surgical system (10). As will be described in greater detail below, uterine manipular (400) and laparoscopic instrument (470) have sensors (462, 464, 474) that communicate to robotic system (10), thereby allowing robotic system (10) to monitor the distance between select components of manipulator (400) and laparoscopic instrument (470), calculate a uterine wall thickness, and/or calculate a pre-determined boundary of acceptable operation which distal end (422) may move within during illustrative use in accordance with the description herein. Further, robotic system (10) may alert a clinician when the distance between certain components of manipulator (400) and instrument (470) indicates over-insertion of distal end (422); and, in instances when uterine manipulator (400) is controlled by robotic arm (16, 110), geofence uterine manipulator (400) to prevent distal end (422) from being over-inserted.

Uterine manipulator (400) may be configured and operable substantially similar to uterine manipulator (300) described above, with differences elaborated below. Uterine manipular (400) thus includes a tool driver interface (410), base (412), a shaft (420), a distal end (422), a balloon (424), a linear portion (426), a curved portion (428), a sleeve (430), a balloon (432), a locking ring (440), and a colpotomy cup (450); which may be substantially similar to tool driver interface (310), base (312), distal end (322), balloon (324), linear portion (326), curved portion (328), sleeve (330), balloon (332), locking ring (340), and colpotomy cup (350) described above, with differences elaborated below.

Base (412) of tool driver interface (410) may be configured to selectively couple with a robotic arm (16, 110). In some instances, robotic arm (16, 110) may be suitably coupled to tool driver interface (410) such that robotic arm (16, 110) merely supports uterine manipulator (400) during use but is still actuated manually by a clinician. In other instances, robotic arm (16, 110) may actuate uterine manipulator (400), either partially or entirely, when tool drive interface (410) is coupled to robotic arm (16, 110). Alternatively, base (412) may be configured for manual control by a clinician such that base (412) is not configured to selectively couple with a robotic arm (16, 110). It should therefore be understood that, in some instances, uterine manipulator (400) may be coupled to a robotic arm (16, 110) of robotic surgical system (10); while in other instances, uterine manipulator (400) may not be coupled to a robotic arm (16, 110) and instead be controlled manually by a clinician during use in accordance with the description herein.

Distal end (422) of shaft (420) includes a distal sensor assembly (460). Distal sensor assembly (460) includes a force detection sensor (462) and a proximity sensor element (464). As will be described in greater detail below, force detection sensor (462) is configured to measure forces imparted on distal end (422) via contact with adjacent anatomical structures; while proximity sensor element (464) is configured to be used in conjunction with a complementary proximity sensor element (474) of laparoscopic instrument (470) in order to measure a distance between sensors (464, 474). In some versions, proximity sensor element (464) comprises a magnet, such that proximity sensor element (464) need not necessarily generate signals within distal sensor assembly (460) in all versions.

Force detection sensor (462) is suitably disposed on distal end (422) of shaft (420) in order to measure forces generated via contact with adjacent anatomical structures, such as the fundus (F) of the uterus (U) or other portions of the uterus (U). Force detection sensor (462) is suitably coupled with a communication wire (466) that extends proximally through shaft (420) and into tool drier interface (410). During an example of use, force detection sensor (462) is in communication with control console (28) via communication wires (466) and/or any other suitable structures as would be apparent to one skilled in the art in view of the teachings herein. Force detection sensor (462) may thus communicate the measured forces acting on distal end (422) to control console (28).

Force detection sensor (462) of the present example is configured to detect when distal end (422) of shaft (420) initially engages the fundus (F) while shaft (420) is initially inserted into uterus (U) in accordance with the description herein; and communicate the detected force to control console (28). As will be described in greater detail below, control console (28) may utilize the measurement of force detection sensor (462) while distal end (422) initially engages the fundus (F) in order to determine a uterine wall thickness and/or to calculate a distal position threshold of uterine manipulator (400). Additionally, control console (28) may use the subsequent real-time force measurements from force detection sensor (462) during use of uterine manipulator (400) to determine if distal end (422) has been over-inserted within uterus (U). Force detection sensor (462) may have any suitable components as would be apparent to one skilled in the art in view of the teachings herein. For example, force detection sensor (462) may include a pressure sensor, a strain-gauge sensor, a multi-axis strain gauge sensor, etc. In some variations, force detection sensor (462) is omitted. It should therefore be understood that some versions of distal sensor assembly (460) that include proximity sensor element (464) may omit force detection sensor (462).

Proximity sensor element (464) is configured to interact with complementary proximity sensor element (474) of laparoscopic instrument (470), such that either or both sensors (464, 474) generate and communicate a corresponding signal to control console (28). Control console (28) may utilize the corresponding signal generated via sensor(s) (464, 474) in order to determine a distance between sensors (464, 474), particularly when distal end (422) is in contact with the fundus (F). Based on the placement of laparoscopic instrument (470), the distance between sensors (464, 474) may be utilized in order to determine a uterine wall thickness and/or to calculate a distal position threshold of uterine manipulator (400). Additionally, the distance between sensor (464, 474) may be monitored in real time to determine if distal end (422) is being over-inserted within uterus (U).

As shown in FIGS. 9A-9E, laparoscopic instrument (470) includes an elongated shaft (472) terminating distally into proximity sensor element (474). Similar to surgical instrument (24, 114) described above, laparoscopic instrument (470) is configured to selectively attach to robotic arm (16, 110) such that robotic surgical system (10) may operatively control laparoscopic instrument (470). In other instances, laparoscopic instrument (470) may be hand-held, but with proximity sensor element (474) still in communication with control console (28). Elongated shaft (472) of laparoscopic instrument (470) is dimensioned to be inserted within a patient laparoscopically such that proximity sensor element (474) may be positioned into engagement with, or directly adjacent to, a superior portion of uterus (U), as shown in the transition from FIG. 9A to FIG. 9B. Placement of elongated shaft (472) may be visually confirmed via a laparoscope.

While in the current example, laparoscopic instrument (470) is shown simplified as an elongated shaft (472) that is coupled to proximity sensor element (474), this is merely optional, as laparoscopic instrument (470) may have any suitable structure as would be apparent to one skilled in the art in view of the teachings herein. In some instances, elongated shaft (472) and/or proximity sensor element (474) may act as a sleeve defining one or more working channels dimensioned to slidably receive working tools, such as graspers, cutters, etc., which may be operatively controlled by robotic arm (16, 110) to which instrument (470) is selectively coupled. In some instances, elongated shaft (472) may also have its own laparoscope incorporated therein, thereby providing visualization of the placement of laparoscopic instrument (470). In some instances, proximity sensor element (474) may be incorporated into an end effector of a laparoscopic instrument, such as jaws of a laparoscopic instrument, thereby allowing proximity sensor element (474) to remain engaged with desired superior portion of uterus (U) during use in accordance with the description herein. As yet another variation, instead of shaft (472) extending through the abdominal wall to the exterior of the patient, laparoscopic instrument (470) may be held and manipulated by a conventional grasper instrument or other secondary laparoscopic instrument.

Proximity sensor elements (464, 474) of uterine manipulator (400) and laparoscopic instrument (470), respectively, may include any suitable components as would be apparent to one skilled in the art in view of the teachings herein. In some instances, only one sensor (464, 474) is in direct communication with control console (28); while in other instances, both sensors (464, 474) may be in direct communication with control console (28).

As one example, one proximity sensor element (464, 474) may include a Hall effect sensor, while the other proximity sensor element (464, 474) includes a magnet. The Hall effect sensor may detect the presence of the magnet and generate a corresponding signal indicative of the distance between Hall effect sensor and the magnet. Further, the Hall effect sensor may communicate that corresponding signal to control console (28), thereby allowing control console (28) to determine a distance between sensors (464, 744). In some such versions, proximity sensor element (464) includes a permanent magnet while proximity sensor element (474) includes a Hall effect sensor. In some other such versions, proximity sensor element (464) includes a Hall effect sensor while proximity sensor element (474) includes a permanent magnet.

As another example, one proximity sensor element (464, 474) may be configured to generate alternating magnetic fields in response to control signals receives by control console (28), while the other proximity sensor element (464, 474) may comprise one or more coils that generate signals in response to the alternating magnetic fields. Such signals may indicate the relative positioning between proximity sensor elements (464, 474). Such signals may be communicated to control console (28) via wire or wirelessly. Control console (28) may process those signals to calculate the spatial positioning and distance between sensors (464, 474).

FIGS. 9A-9E shows an example of an anchoring process of uterine manipulator (400) in coordination with laparoscopic instrument (470) and robotic surgical system (10); while FIG. 10 shows an example of a method (1000) used by control console (28) of robotic surgical system (10) to measure the uterine thickness and/or calculate a distal position boundary/threshold for distal end (422) of uterine manipulator (400) during use in accordance with the description herein. First, as shown between FIGS. 9A-9B, laparoscopic instrument (470) may be advanced until proximity sensor element (474) reaches suitable engagement with the exterior of the uterus (U). In particular, proximity sensor element (474) is directly adjacent to an exterior of uterus (U) that is superior to fundus (F). Such advancement may be visually confirmed laparoscopically via an endoscope.

As shown in FIG. 10, in instances where laparoscopic instrument (470) is operatively coupled to a robotic arm (16, 110) of robotic surgical system (10), control console (28) may instruct such a robotic arm (16, 110) to advance (1002) laparoscopic sensor (474) into engagement with the exterior of uterus (U). In cases where a robotic arm (16, 110) of robotic surgical system (10) is robotically positioning laparoscopic instrument (470), control console (28) may rely on the laparoscopic image, force feedback, kinematic data, and/or any other suitable data source(s) to determine when the distal end of laparoscopic instrument (470) has sufficiently engaged the uterus (U). In cases where a clinician is manually positioning laparoscopic instrument (470), the clinician may rely on one or both of laparoscopic imaging and/or tactile feedback to determine when the distal end of laparoscopic instrument (470) has sufficiently engaged the uterus (U). In either scenario, proximity sensor element (474) acts as a reference point for the portion of uterus (U) in contact with proximity sensor element (474). In some instances, proximity sensor element (474) may be positioned directly adjacent to the exterior of uterus (U) without directly engaging uterus (U). It should also be understood that proximity sensor element (474) may be positioned proximally from the distal tip of shaft (472) in some versions, at a fixed and known distance from the distal tip of shaft (472).

Next, as also shown in FIG. 10, after suitable placement of laparoscopic sensor (474), control console (28) may calculate the position of laparoscopic sensor (1004) using any suitable means as would be apparent to one skilled in the art in view of the teachings herein.

Turning back to FIG. 9C, once laparoscopic instrument (470) is suitably positioned, distal end (422) of uterine manipulator (400) is advanced though vaginal entry point (VEP), through vagina (V), and into uterus (U). Advancement of uterine manipular (400) may be manual or robotically controlled. In particular, distal end (422) is advanced until force detection sensor (462) makes suitable contact with fundus (F). Force detection sensor (464) communicates the contact force generated from engagement with fundus (F) to control console (28).

As shown in FIG. 10, control console (28) determines (1006) that engagement has occurred between force detection sensor (462) and fundus (F) via data from force detection sensor (462). In some versions, control console (28) may calculate a pressure value imparted on force detection sensor (474) via fundus (F). If the calculated pressure is within a pre-determined range associated with acceptable contact between distal (422) and fundus (F), control console (28) may then receive and accept (1008) a signal from one or both of proximity sensor elements (464,474), as such a signal from one or both of proximity sensor elements (464, 474) may indicate the distance between proximity sensor elements (464, 474); which may in turn indicate the wall thickness of the uterus (U) in the region of the fundus (F). If the calculated pressure is too great (or the distance between sensor (464, 474) is too small) compared to the predetermined suitable pressure range, this may indicate that the fundus (F) is being substantially deformed by distal end (422), such that the distance between proximity sensor elements (464, 474) does not accurately indicate the wall thickness of the uterus (U) in the region of the fundus (F). In such scenarios, control console (28) may alert a clinician that distal end (422) needs to be adjusted accordingly. The use of force detection sensor (462) to determine suitable engagement with fundus (F) may replace the conventional sounding process that may otherwise be performed with a specialized sounding instrument.

In versions where force detection sensor (462) is omitted, a clinician may rely on tactile feedback to determine when distal end (422) has made suitable contact with fundus (F); and then provide an input to control console (28) to indicate that distal end (422) has made suitable contact with fundus (F). In response to such input, control console (28) may receive and accept (1008) a signal from one or both of proximity sensor elements (464,474), as such a signal from one or both of proximity sensor elements (464, 474) may indicate the distance between proximity sensor elements (464, 474); which may in turn indicate the wall thickness of the uterus (U) in the region of the fundus (F).

Control console (38) may further utilize (1010) the received signal from one or both of proximity sensor elements (464, 474) to calculate the uterine wall thickness and/or a threshold/boundary which distal end (422) of uterine manipulator (400) may be actuated within. With proximity sensor element (474) suitably posited on an exterior of uterus (U), uterine wall thickness may be represented by the distance between sensors (464, 474) while in the position shown in FIG. 9C. The threshold boundary may define an acceptable distance between proximity sensor elements (464, 474) while laparoscopic proximity sensor element (474) is suitably positioned relative to uterus (U). Therefore, robotic system (10) may monitor the distance between sensors (464, 474) during use of uterine manipulator (400) in order to determine if distal end (422) has been over-inserted. In calculating the threshold boundary for distal end (422), control console (28) may utilize any suitable data as would be apparent to one skilled in the art in view of the teachings herein. For example, control console (28) may utilize the uterine wall thickness, pressure calculated from force detection sensor (474), preloaded data and algorithms utilizing pre-determined empirical data associated with over-insertion, etc.

Figure 9A:
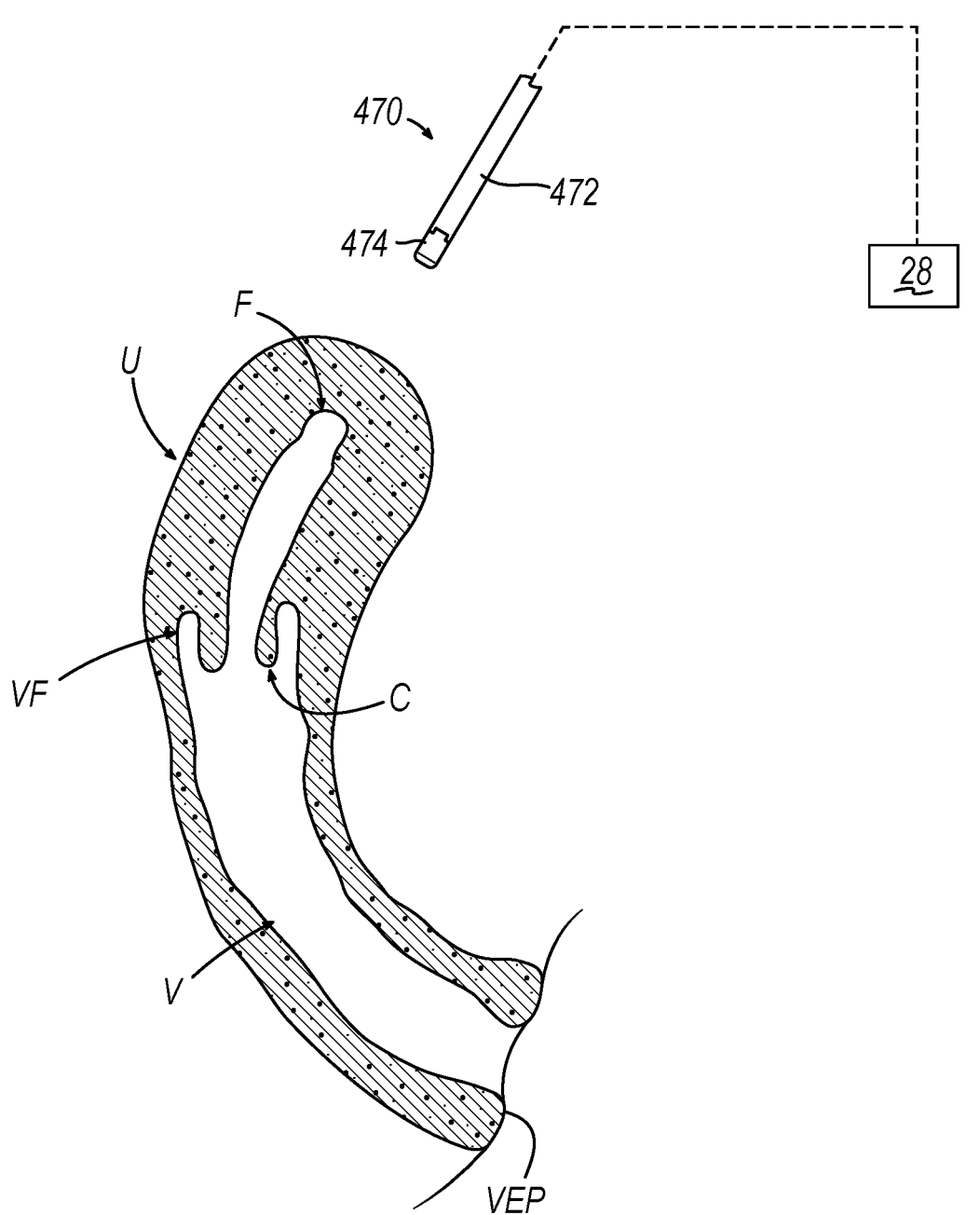
FIG. 9A depicts a mid-sagittal cross-sectional view of a vagina and uterus, with a laparoscopic instrument being introduced from a laparoscopic side.
Figure 9B:
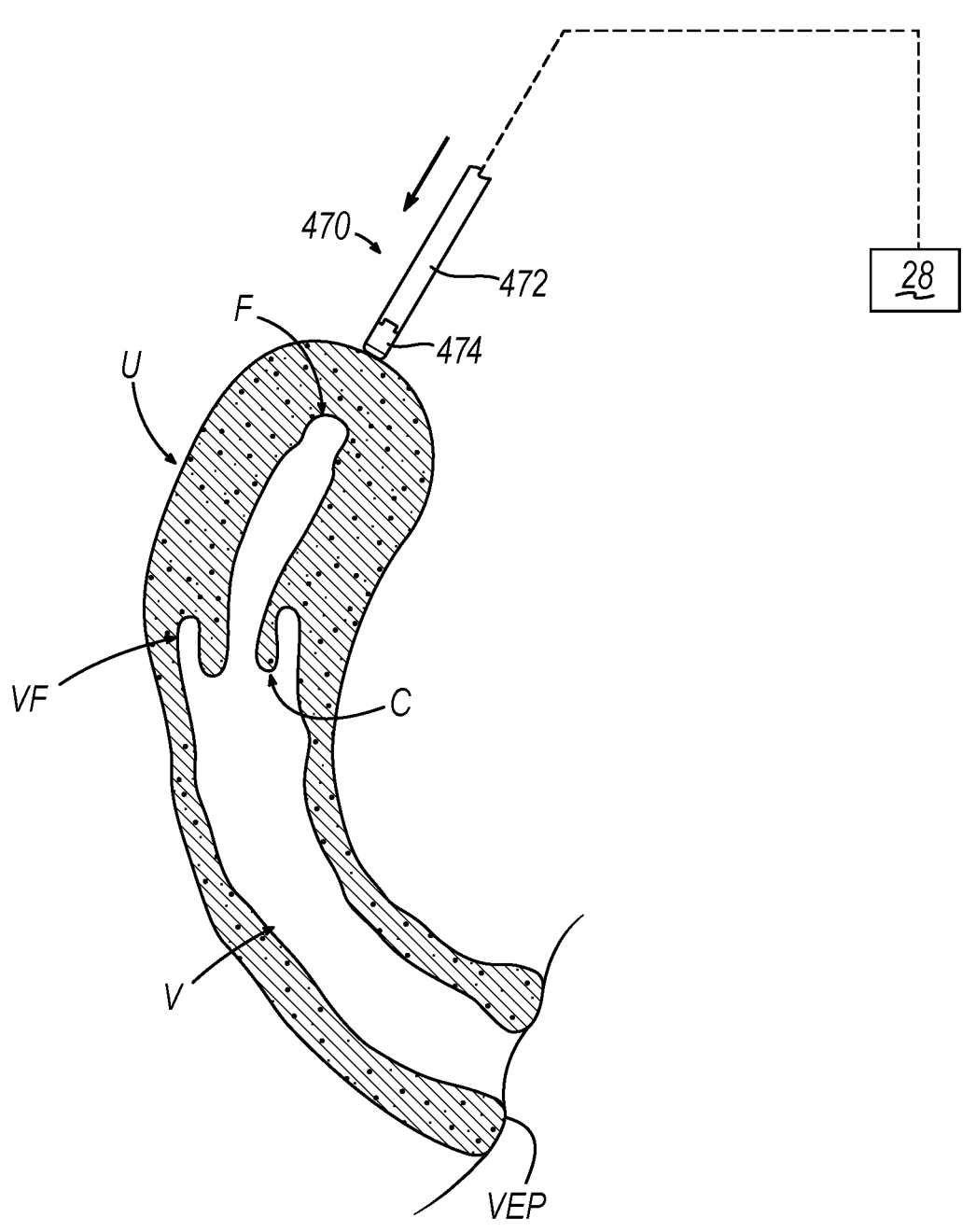
FIG. 9B depicts a mid-sagittal cross-sectional view of the vagina and uterus of FIG. 9A, with the laparoscopic instrument of FIG. 9A positioned to engage a superior portion of the uterus directly adjacent to the laparoscopic side.
Figure 9C:
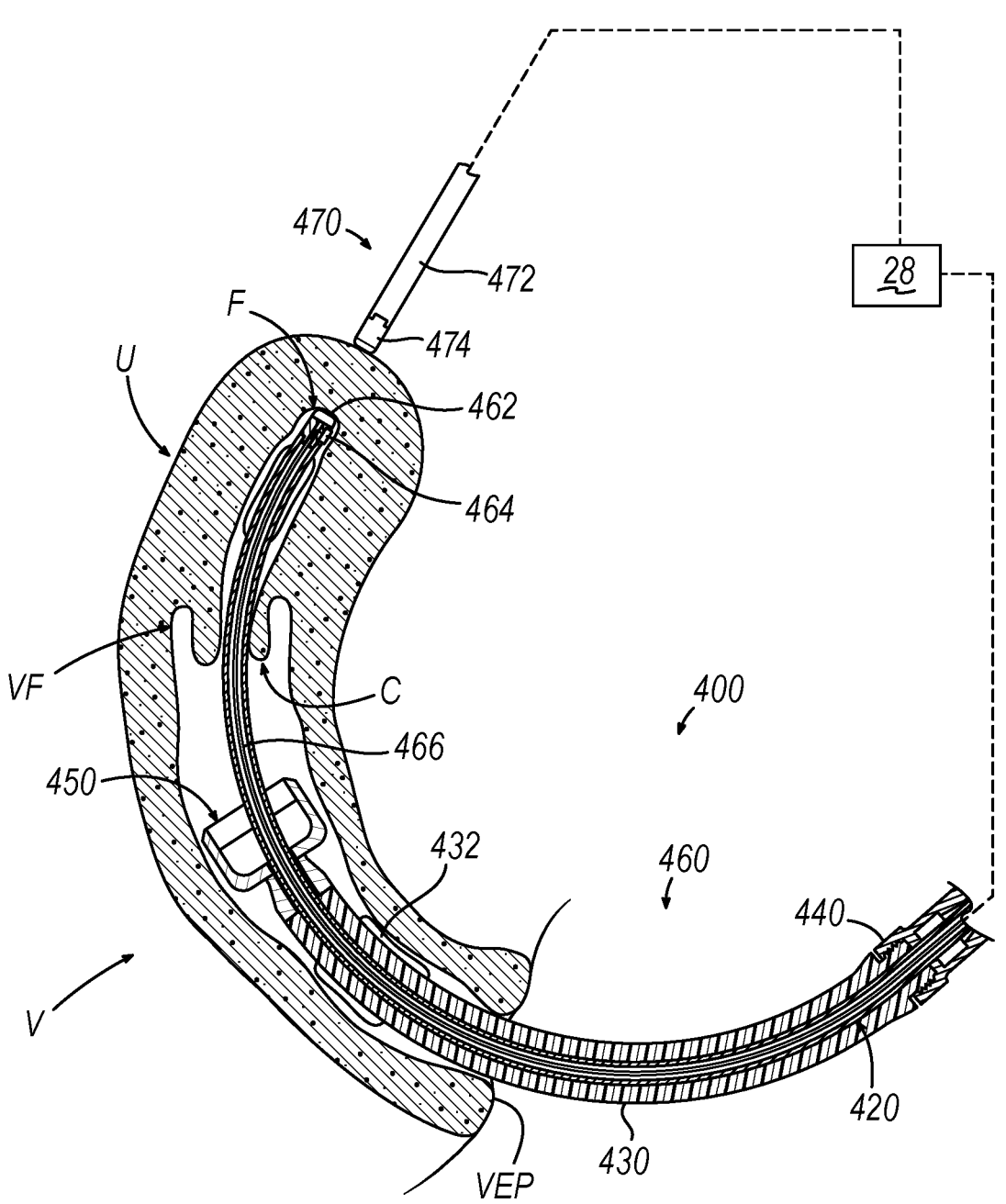
FIG. 9C depicts a mid-sagittal cross-sectional view of the vagina and uterus of FIG. 9A, with the laparoscopic instrument of FIG. 9A engaged with the superior portion of the uterus directly adjacent to the laparoscopic side, with the shaft of the uterine manipulator instrument of FIG. 8 inserted through the vagina into the uterus into initial engagement with the fundus.
Figure 9D:
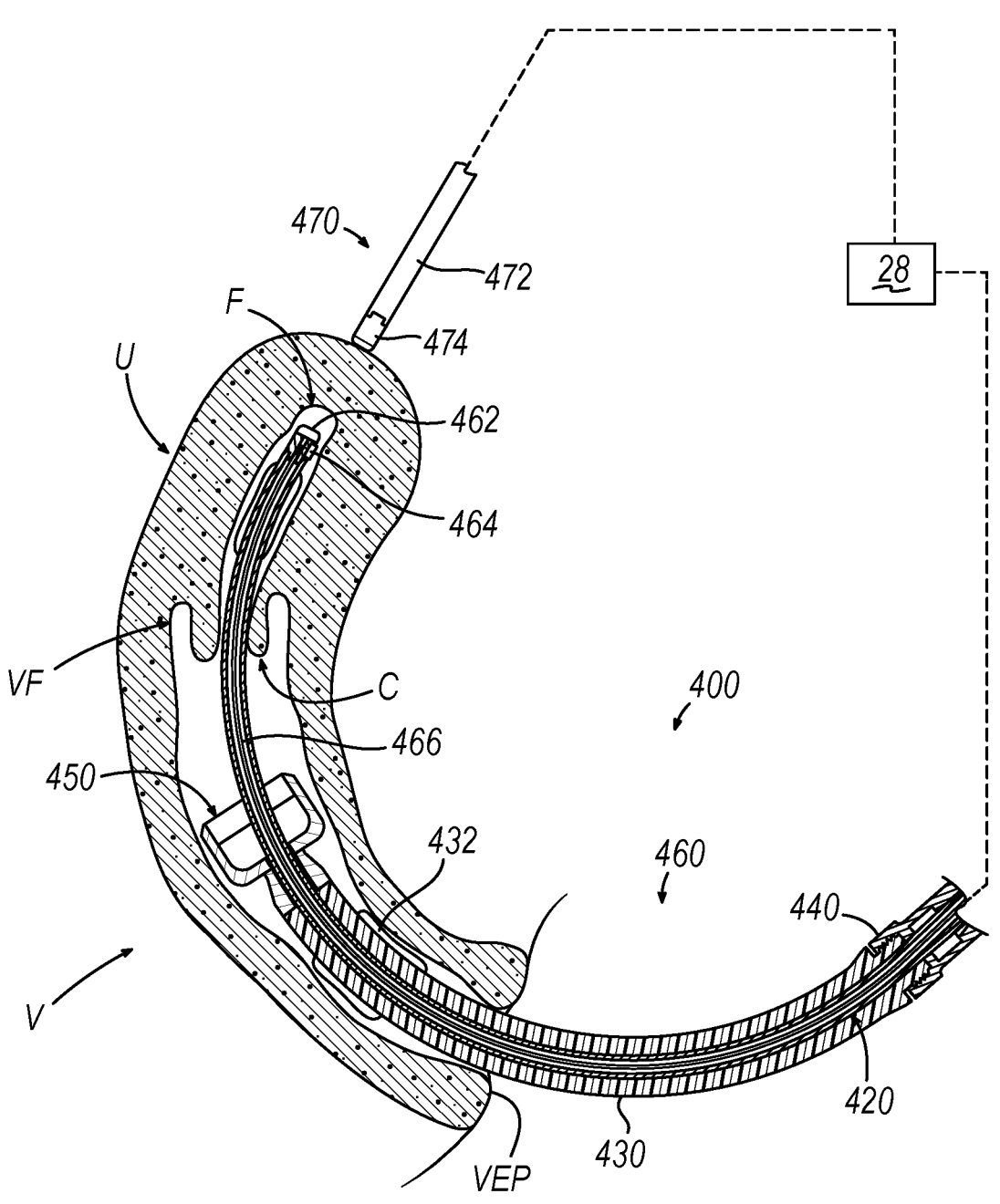
FIG. 9D depicts a mid-sagittal cross-sectional view of the vagina and uterus of FIG. 9A, with the laparoscopic instrument of FIG. 9A engaged with the superior portion of the uterus directly adjacent to the laparoscopic side, with the shaft of the uterine manipulator instrument of FIG. 8 retracted from engagement with the fundus.
Figure 9E:
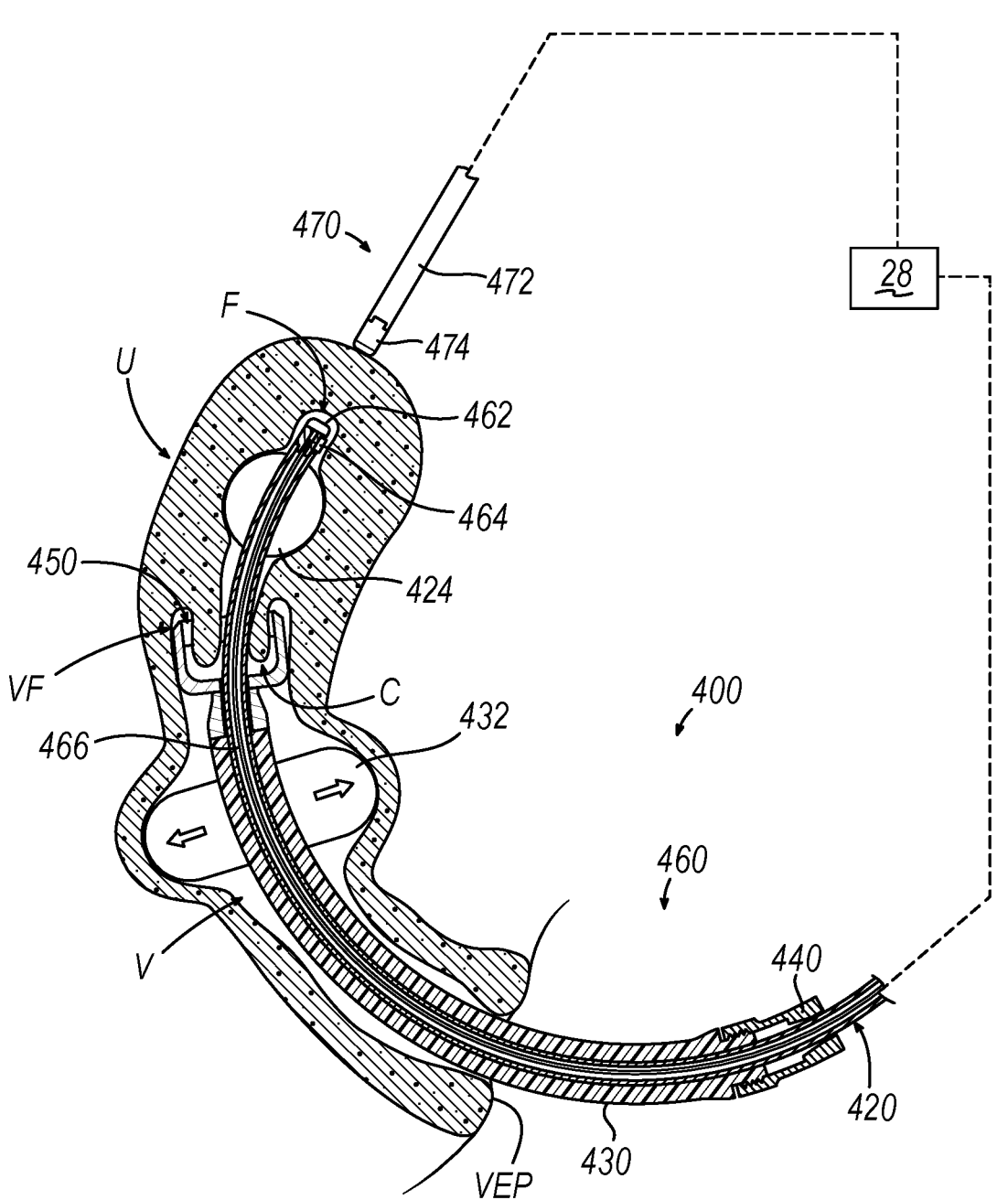
FIG. 9E depicts a mid-sagittal cross-sectional view of the vagina and uterus of FIG. 9A, with the laparoscopic instrument of FIG. 9A engaged with the superior portion of the uterus directly adjacent to the laparoscopic side, with a balloon of the uterine manipulator instrument of FIG. 8 in the inflated state, with a sleeve of the uterine manipulator instrument in a distal position such that a colpotomy cup of the sleeve is engaged with the cervix, and with a balloon of the sleeve in an inflated state.

As shown between FIG. 9C-9D, once uterine wall thickness and the boundary have been suitably calculated, in some instances distal end (422) may be proximally retracted out of engagement with fundus (F) in preparation of being suitably anchored to uterus (U) in accordance with the description herein. Next as shown in FIG. 9E, uterine manipulator (400) may be anchored to suitable anatomical structures in substantially similar manner shown above with uterine manipulator (300). With uterine manipulator (400) anchored to uterus (U), uterine manipulator (400) may now be configured to suitably position and orient uterus (U) to facilitate the operations being performed.

Figure 11:
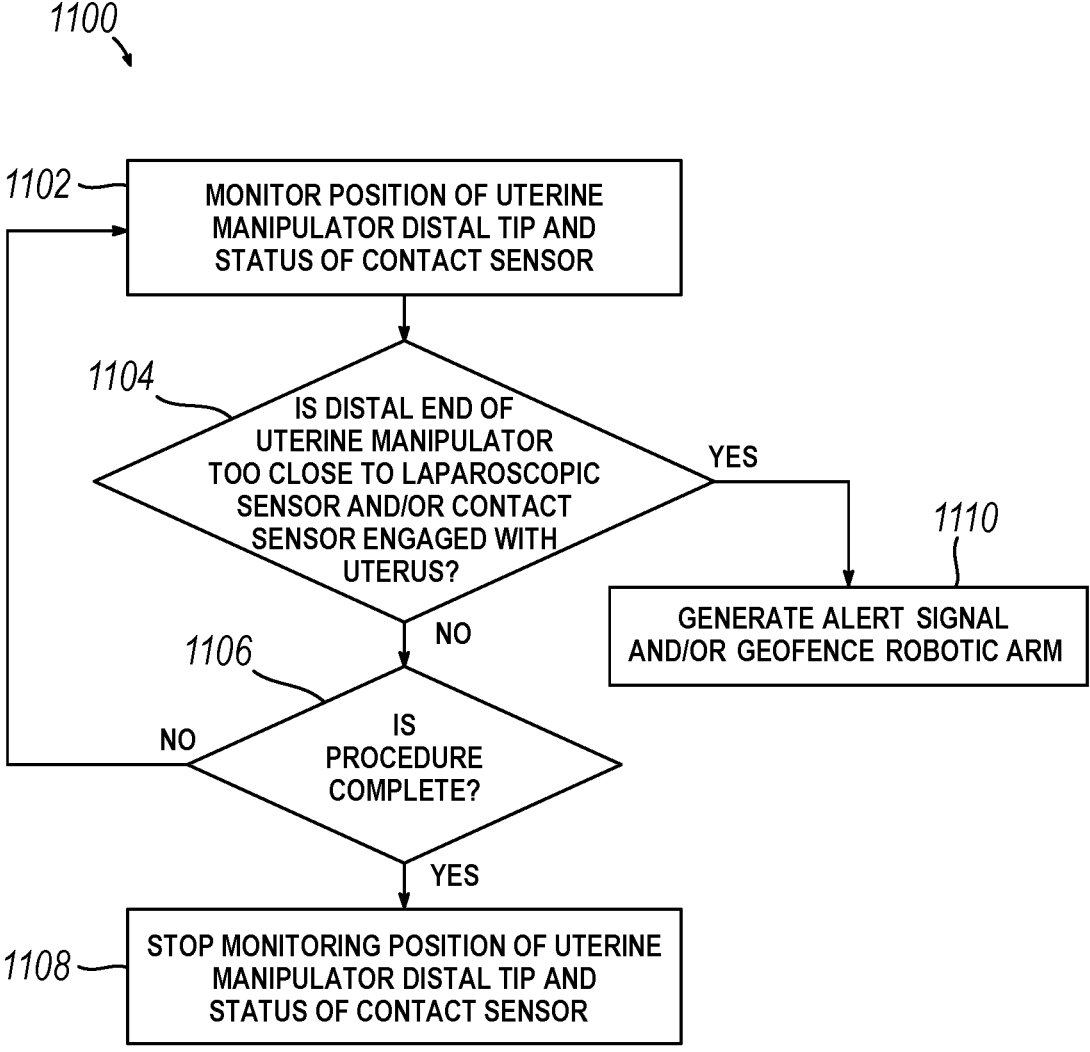
FIG. 11 depicts a flowchart of an example of a method for the control console of the table-based robotic system of FIG. 1 to monitor the distance between the laparoscopic instrument of FIG. 9A and the uterine manipulator instrument of FIG. 8.

FIG. 11 shows an example of a method (1100) that may be executed via control console (28), and/or other suitable components of robotic surgical system (10), to monitor the position of distal end (422) during use of uterine manipulator (400) to position and orient uterus (U) after the anchoring method (1000) described above. During such use, distal end (422) may be actuated in order to move uterus (U) into desirable positions and orientations. During such movement, proximity sensor element (474) may remain in substantially the same position as shown in FIGS. 9B-9E, and/or may be actuated to remain engaged with the same superior portion of uterus (U) as shown in FIGS. 9B-9E. As distal end (422) is moved in accordance with the description herein, control console (28) monitors (1102) the distance between proximity sensor elements (464, 474) in real time. In versions where force detection sensor (462) is included, control console (28) may further monitor (1102) any force-indicative signals from force detection sensor (462) in real time.

While control console (28) monitors sensors (462, 464, 474), control console (28) processes the data to determine (1104) if distal end (422) of uterine manipulator (400) is too close to laparoscopic sensor (474) and/or if force detection sensor (462) is receiving too much reactionary force from adjacent anatomy of uterus (U). If control console (28) determines the distance between the two proximity sensor elements (464, 474) is too close, this may indicate that distal end (422) is positioned adjacent and/or past the calculated threshold boundary, which may be an indication that distal end (422) has been over-inserted. Similarly, if control console (28) determines that force sensor (462) is measuring too much force against adjacent anatomy of uterus (U), this may also be an indication that distal end (422) has been over-inserted. In such circumstances, control console (28) generates (1110) instructions for robotic control system (10) to issue an alert signal, indicating to the clinician that distal end (422) is close to being over-inserted. Any suitable alert signal may be generated as would be apparent to one skilled in the art in view of the teachings herein. For example, an audible tone, emitted light, tactile feedback, visual representation on a screen, etc., may be used to alert the clinician.

In instances where a robotic arm (16, 110) is utilized to control the position of uterine manipulator (400), control console (28) may geofence distal end (422) from being over-inserted out of the calculated threshold boundary. In other words, control console (28) may inhibit robotic arm (16, 110) from actuating distal end (422) out of the calculated threshold boundary. Therefore, if a clinician provides instructions to actuate robot arm (16, 110) and uterine manipulator (400) to a position where distal end (422) would be over-inserted, control console (28) may filter such commands, thereby preventing over-insertion of distal end (422).

It should be understood that in instances where uterine manipulator (400) is controlled by a robotic arm (16, 110), some versions of robotic surgical system (10) may not be able to accurately measure the distance between distal end of laparoscopic instruments (470) and the distal end (422) of uterine manipulator (400) utilizing a kinematic chain. For example, the accumulated tolerance errors (i.e., a tolerance stack) in measuring the position of each link (116) and joint (118) when determining the global position of distal end (422) relative to laparoscopic instrument (470) may be too great to provide accurate relative positioning data in some versions of robotic surgical system (10). Therefore, utilizing proximity sensor elements (464, 474) may alleviate this tolerance stack and provide accurate positioning data of distal end (422) relative to the fundus (F) of the uterus (U).

If control console (28) determines (1104) that distal end (422) of uterine manipulator (400) is not too close to proximity sensor element (474) and/or force detection sensor (462) is not overly engaged with adjacent anatomy of uterus (U), control console (28) may ask the clinician if the procedure is complete (1106). If not, control console (28) may continue monitoring (1102). If the procedure is complete, control console (28) may stop monitoring (1108) signals from sensors (462, 464, 474).

IV. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system, comprising: (a) a control console; (b) a laparoscopic instrument comprising a first proximity sensor element; and (c) a uterine manipulator, wherein the uterine manipulator comprises: (i) a base, and (ii) a shaft extending distally from the base, wherein the shaft comprises: (A) a distal end dimensioned to be inserted into a uterus of a patient, and (B) a second proximity sensor element located at the distal end, and wherein the first proximity sensor element and the second proximity sensor element are configured to cooperatively generate a distance signal indicating a distance between the first proximity sensor element and the second proximity sensor element, wherein the control console is configured to receive the distance signal from either the first proximity sensor element or the second proximity sensor element and calculate a corresponding distance between the first proximity sensor element and the second proximity sensor element, wherein the control console is configured to compare the corresponding distance with a threshold distance and generate an alert signal when the corresponding distance is smaller than the threshold distance.

Example 2

The system of Example 1, wherein the control console is configured to calculate the threshold distance utilizing at least one measured parameter.

Example 3

The system of Example 2, wherein the at least one measured parameter comprises a uterine wall thickness measured by the first proximity sensor element and the second proximity sensor element.

Example 4

The system of any of Examples 2 through 3, wherein the shaft further comprises a force sensor located at the distal end of the shaft, wherein the force sensor is in communication with the control console.

Example 5

The system of Example 4, wherein the at least one measured parameter comprises a force signal generated by the force sensor.

Example 6

The system of Example 5, wherein the at least one measured parameter comprises a uterine wall thickness measured by the first proximity sensor element and the second proximity sensor element combined with the force signal generated by the force sensor.

Example 7

The system of any of Examples 4 through 6, wherein the control console is configured to generate the alert signal in response to the force sensor measuring a force past a predetermined force threshold.

Example 8

The system of any of Examples 1 through 7, further comprising a first robotic arm in communication with the control console, wherein the laparoscopic instrument is operatively coupled with the first robotic arm.

Example 9

The system of Example 8, further comprising a second robotic arm in communication with the control console, wherein the uterine manipulator is operatively coupled with the second robotic arm.

Example 10

The system of Example 9, wherein the control console is configured to geofence movement of the second robotic arm and the uterine manipulator in response to the corresponding distance being smaller than the threshold distance.

Example 11

The system of Example 10, wherein the base is configured to selectively couple with the second robotic arm.

Example 12

The system of any of Examples 1 through 11, wherein the uterine manipulator further comprises a colpotomy cup slidably attached to the shaft.

Example 13

The system of Example 12, wherein the uterine manipulator further comprises a locking ring configured to selectively fix the colpotomy cup relative to the shaft.

Example 14

The system of Example 13, wherein the uterine manipulator further comprises a sleeve extending between the locking ring and the colpotomy cup.

Example 15

The system of any of Examples 1 through 14, wherein the shaft further comprises an anchoring balloon.

Example 16

A robotic surgical system, comprising: (a) a control console; (b) a first robotic arm in communication with the control console; (c) a laparoscopic instrument configured to selectively couple with the first robotic arm, wherein the laparoscopic instrument comprises a first proximity sensor element; and (d) a uterine manipulator, wherein the uterine manipulator comprises: (i) a base, and (ii) a shaft extending distally from the base, wherein the shaft comprises: (A) a distal end dimensioned to be inserted into a uterus of a patient; and (B) a second proximity sensor element located at the distal end, and wherein the first proximity sensor element and the second proximity sensor element are configured to cooperatively generate a distance signal, wherein the control console is configured to receive the distance signal from either the first proximity sensor element or the second proximity sensor element and calculate a corresponding distance between the first proximity sensor element and the second proximity sensor element, wherein the control console is configured to generate an alert signal when the corresponding distance is smaller than a predetermined distance.

Example 17

The system of Example 16, further comprising a second robotic arm in communication with the control console, wherein the second robotic arm is configured to selectively couple with the base of the uterine manipulator.

Example 18

The system of any of Examples 16 through 17, further comprising a second robotic arm in communication with the control console, wherein the control console is configured to restrict movement of the second robotic arm to thereby prevent second robotic arm from moving the distal end of the shaft to a position where a distance between the first proximity sensor element and the second proximity sensor element is smaller than the predetermined distance.

Example 19

The system of any of Example 16 through 18, wherein the shaft further comprises a force sensor associated with the distal end.

Example 20

A method of generating an alert signal, the method comprising: (a) receiving a distance signal generated by proximity sensing arrangement formed by a first proximity sensor element and a second proximity sensor, wherein the first proximity sensor element is positioned outside of a uterus, wherein the second proximity sensor element is located within an interior of the uterus; (b) utilizing the distance signal to calculate a first distance; (c) comparing the first distance with a predetermined threshold; and (d) generating the alert signal if the first distance is smaller than the predetermined threshold.

V. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components.

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those skilled in the art.

While the examples herein are described mainly in the context of uterine manipulator instruments, it should be understood that various teachings herein may be readily applied to a variety of other types of devices. By way of example only, the various teachings herein may be readily applied to other types of surgical instruments including tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those skilled in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system, comprising:
(a) a control console;
(b) a laparoscopic instrument comprising a first proximity sensor element; and
(c) a uterine manipulator, wherein the uterine manipulator comprises:
  (i) a base, and
  (ii) a shaft extending distally from the base, wherein the shaft comprises:
    (A) a distal end dimensioned to be inserted into a uterus of a patient, and
    (B) a second proximity sensor element located at the distal end, and
wherein the first proximity sensor element and the second proximity sensor element are configured to cooperatively generate a distance signal indicating a distance between the first proximity sensor element and the second proximity sensor element,
wherein the control console is configured to receive the distance signal from either the first proximity sensor element or the second proximity sensor element and calculate a corresponding distance between the first proximity sensor element and the second proximity sensor element,
wherein the control console is configured to compare the corresponding distance with a threshold distance and generate an alert signal when the corresponding distance is smaller than the threshold distance,
wherein the control console is configured to calculate the threshold distance utilizing at least one measured parameter, wherein the at least one measured parameter comprises a uterine wall thickness measured by the first proximity sensor element and the second proximity sensor element.

2. The system of claim 1, wherein the shaft further comprises a force sensor located at the distal end of the shaft, wherein the force sensor is in communication with the control console.

3. The system of claim 2, wherein the at least one measured parameter comprises a force signal generated by the force sensor.

4. The system of claim 3, wherein the at least one measured parameter comprises a uterine wall thickness measured by the first proximity sensor element and the second proximity sensor element combined with the force signal generated by the force sensor.

5. The system of claim 2, wherein the control console is configured to generate the alert signal in response to the force sensor measuring a force past a predetermined force threshold.

6. The system of claim 1, further comprising a first robotic arm in communication with the control console, wherein the laparoscopic instrument is operatively coupled with the first robotic arm.

7. The system of claim 6, further comprising a second robotic arm in communication with the control console, wherein the uterine manipulator is operatively coupled with the second robotic arm.

8. The system of claim 7, wherein the control console is configured to geofence movement of the second robotic arm and the uterine manipulator in response to the corresponding distance being smaller than the threshold distance.

9. The system of claim 8, wherein the base is configured to selectively couple with the second robotic arm.

10. The system of claim 1, wherein the uterine manipulator further comprises a colpotomy cup slidably attached to the shaft.

11. The system of claim 10, wherein the uterine manipulator further comprises a locking ring configured to selectively fix the colpotomy cup relative to the shaft.

12. The system of claim 11, wherein the uterine manipulator further comprises a sleeve extending between the locking ring and the colpotomy cup.

13. The system of claim 1, wherein the shaft further comprises an anchoring balloon.

14. A robotic surgical system, comprising:
(a) a control console;
(b) a laparoscopic instrument, wherein the laparoscopic instrument comprises a first proximity sensor element; and
(c) a uterine manipulator, wherein the uterine manipulator comprises:
(i) a base, and
(ii) a shaft extending distally from the base, wherein the shaft comprises:
(A) a distal end dimensioned to be inserted into a uterus of a patient,
(B) a second proximity sensor element located at the distal end, and,
(C) a force sensor located at the distal end of the shaft, wherein the force sensor is in communication with the control console,
wherein the first proximity sensor element and the second proximity sensor element are configured to cooperatively generate a distance signal,
wherein the control console is configured to receive the distance signal from either the first proximity sensor element or the second proximity sensor element and calculate a corresponding distance between the first proximity sensor element and the second proximity sensor element,
wherein the control console is configured to generate an alert signal when the corresponding distance is smaller than a predetermined distance,
wherein the control console is configured to calculate the predetermined distance utilizing at least one measured parameter,
wherein the at least one measured parameter comprises a force signal generated by the force sensor.

15. The system of claim 14, wherein the at least one measured parameter comprises a uterine wall thickness measured by the first proximity sensor element and the second proximity sensor element combined with the force signal generated by the force sensor.

16. The system of claim 14, wherein the control console is configured to generate the alert signal in response to the force sensor measuring a force past a predetermined force threshold.

17. The system of claim 14, further comprising a first robotic arm in communication with the control console, and wherein the laparoscopic instrument is configured to selectively couple with the first robotic arm.

18. The system of claim 17, further comprising a second robotic arm in communication with the control console, wherein the second robotic arm is configured to selectively couple with the base of the uterine manipulator.

19. The system of claim 17, further comprising a second robotic arm in communication with the control console, wherein the control console is configured to restrict movement of the second robotic arm to thereby prevent second robotic arm from moving the distal end of the shaft to a position where a distance between the first proximity sensor element and the second proximity sensor element is smaller than the predetermined distance.

20. A robotic surgical system, comprising:
(a) a control console;
(b) a laparoscopic instrument, wherein the laparoscopic instrument comprises a first proximity sensor element; and
(c) a uterine manipulator, wherein the uterine manipulator comprises:
(i) a base, and
(ii) a shaft extending distally from the base, wherein the shaft comprises:
(A) a distal end dimensioned to be inserted into a uterus of a patient, and
(B) a second proximity sensor element located at the distal end, and,
wherein the first proximity sensor element and the second proximity sensor element are configured to cooperatively generate a distance signal,
wherein the control console is configured to receive the distance signal from either the first proximity sensor element or the second proximity sensor element and calculate a corresponding distance between the first proximity sensor element and the second proximity sensor element,
wherein the control console is configured to generate an alert signal when the corresponding distance is smaller than a predetermined distance,
wherein the control console is configured to calculate the predetermined distance utilizing at least one measured parameter, wherein the at least one measured parameter comprises a uterine wall thickness measured by the first proximity sensor element and the second proximity sensor element.

*   *   *   *   *